US009629790B2

(12) United States Patent
Lundberg et al.

(10) Patent No.: US 9,629,790 B2
(45) Date of Patent: Apr. 25, 2017

(54) STABILIZATION OF COSMETIC COMPOSITIONS

(75) Inventors: Brock Lundberg, Roberts, WI (US); Olivia Richardson, Minneapolis, MN (US); Laura Valverde, St. Paul, MN (US)

(73) Assignee: FIBERSTAR, INC, River Falls, WI (US)

( * ) Notice: Subject to any disclaimer, the term of this patent is extended or adjusted under 35 U.S.C. 154(b) by 613 days.

(21) Appl. No.: 12/459,452

(22) Filed: Jun. 30, 2009

(65) Prior Publication Data

US 2009/0269376 A1 Oct. 29, 2009

Related U.S. Application Data

(63) Continuation-in-part of application No. 11/440,603, filed on May 25, 2006, now abandoned, which is a continuation-in-part of application No. 10/969,805, filed on Oct. 20, 2004, now abandoned, which is a continuation-in-part of application No. 10/288,793, filed on Nov. 6, 2002, now Pat. No. 7,094,317.

(51) Int. Cl.
| | |
|---|---|
| *A61K 8/73* | (2006.01) |
| *A61Q 19/00* | (2006.01) |
| *A61Q 5/12* | (2006.01) |
| *A61Q 9/02* | (2006.01) |
| *A61Q 15/00* | (2006.01) |

(52) U.S. Cl.
CPC .............. *A61K 8/731* (2013.01); *A61Q 19/00* (2013.01); *A61Q 5/12* (2013.01); *A61Q 9/02* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 4,209,536 A | 6/1980 | Dogliotti | |
| 4,232,049 A | 11/1980 | Blake | |
| 4,294,653 A | 10/1981 | Lindahl et al. | |
| 4,374,702 A | 2/1983 | Turbak et al. | |
| 4,413,017 A | 11/1983 | Loader | |
| 4,613,508 A | 9/1986 | Shishido | |
| 4,629,575 A | 12/1986 | Weibel | |
| 4,752,493 A | 6/1988 | Moriki | |
| 4,774,099 A | 9/1988 | Feeney et al. | |
| 4,806,475 A | 2/1989 | Gould | |
| 4,831,127 A | 5/1989 | Weibel | |
| 4,834,996 A | 5/1989 | Fazzolare et al. |
| 4,873,093 A | 10/1989 | Fazzolare et al. |
| 4,923,981 A | 5/1990 | Weibel et al. |
| 4,957,599 A | 9/1990 | Chou et al. |
| 4,972,037 A | 11/1990 | Garbe et al. |
| 4,981,902 A | 1/1991 | Mitra et al. |
| 4,981,903 A | 1/1991 | Garbe et al. |
| 5,000,968 A | 3/1991 | Szwerc et al. |
| 5,190,776 A | 3/1993 | Baumann |
| 5,209,924 A | 5/1993 | Garbe et al. |
| 5,219,560 A | 6/1993 | Suzuki et al. |
| 5,342,636 A | 8/1994 | Bakshi et al. |
| 5,360,627 A | 11/1994 | Desai et al. |
| 5,385,640 A | 1/1995 | Weibel et al. |
| 5,403,610 A | 4/1995 | Murphy et al. |
| 5,419,925 A | 5/1995 | Seiden et al. |
| 5,429,834 A | 7/1995 | Addesso et al. |
| 5,439,697 A | 8/1995 | Gonzalez-Sanz |
| 5,468,477 A | 11/1995 | Kumar et al. |
| 5,487,419 A | 1/1996 | Weibel |
| 5,500,240 A | 3/1996 | Addesso et al. |
| 5,625,005 A | 4/1997 | Mallya et al. |
| 5,658,609 A | 8/1997 | Abboud et al. |
| 5,725,882 A | 3/1998 | Kumar et al. |
| 5,766,662 A | 6/1998 | Inglett |
| 5,817,381 A | 10/1998 | Chen et al. |
| 5,849,318 A | 12/1998 | Imai et al. |
| 5,964,983 A | 10/1999 | Dinand et al. |

(Continued)

FOREIGN PATENT DOCUMENTS

| | | |
|---|---|---|
| EP | 096459 | 12/1983 |
| EP | 0102829 | 3/1984 |

(Continued)

OTHER PUBLICATIONS

Gu et al. Structure-function relationships of highly refined cellulose. Transactions of the American Society of Agricultural Engineers (2001) vol. 44(6): 1707-1712.*

(Continued)

*Primary Examiner* — Bethany Barham
*Assistant Examiner* — Peter Anthopolos
(74) *Attorney, Agent, or Firm* — Mark A. Litman & Associates, P.A.

(57) ABSTRACT

A composition of matter is used as an ingredient in cosmetics comprising at least 0.5% by weight and preferably 1-30% by weight of highly refined cellulose fiber in a cosmetic composition. Additionally present in the composition are other conventional cosmetic ingredients as known in the art. This composition may include at least colorants (dyes and pigments), lipophilic materials, aqueous materials (water and aqueous solutions), waxes, binding agents (polymers, thickening agents), emollients, emulsifiers, thickening agents, antioxidants, natural and synthetic oils and extracts, clays, ultraviolet radiation absorbers, and the like.

4 Claims, No Drawings

(56) References Cited

U.S. PATENT DOCUMENTS

| | | | |
|---|---|---|---|
| 6,048,564 | A | 4/2000 | Young et al. |
| 6,083,582 | A | 7/2000 | Chen et al. |
| 6,231,913 | B1 | 5/2001 | Schwimmer et al. |
| 6,251,458 | B1 | 6/2001 | Weibel |
| 6,479,090 | B1 | 11/2002 | Carey et al. |
| 6,506,435 | B1 | 1/2003 | Lundberg et al. |
| 6,534,071 | B1 * | 3/2003 | Tournilhac et al. .......... 424/401 |
| 6,645,546 | B2 | 11/2003 | Roney et al. |
| 7,074,300 | B2 | 7/2006 | Lundberg et al. |
| 2002/0012722 | A1 | 1/2002 | Prosise et al. |
| 2002/0060382 | A1 | 5/2002 | Luo et al. |
| 2003/0116289 | A1 | 6/2003 | Lundberg et al. |
| 2003/0144245 | A1 | 7/2003 | Addis et al. |
| 2004/0062851 | A1 | 4/2004 | Bender et al. |
| 2004/0086626 | A1 | 5/2004 | Lundberg et al. |
| 2005/0074542 | A1 | 4/2005 | Lundberg et al. |
| 2005/0233044 | A1 | 10/2005 | Rader et al. |
| 2005/0271790 | A1 | 12/2005 | Aronson et al. |
| 2005/0274469 | A1 | 12/2005 | Lundberg et al. |

FOREIGN PATENT DOCUMENTS

| | | |
|---|---|---|
| EP | 337653 | 10/1989 |
| EP | 0388582 | 9/1990 |
| EP | 0815836 | 1/1998 |
| EP | 0895467 | 2/1999 |
| FR | 0113920 | 5/2003 |
| WO | WO9735541 | 10/1997 |
| WO | WO0132978 | 5/2001 |
| WO | WO03030916 | 4/2003 |

OTHER PUBLICATIONS

Marin et al. By-products from different citrus processes as a source of customized functional fibres. Food Chemistry 100 (2007) 736-741 (electronically published Dec. 19, 2005).*

Haard and Chism, "Characteristics of Edible Plant Tissues," 1996, Food Chemistry. pp. 944-1011; Ed. By Fennema. Marcel Dekker NY, NY.

Gu, L., R Ruan, P. Chen, W. Wilcke, P. Addis. 2001. Structure Function Relationships of Highly Refined Cellulose. Transactions of the ASAE. vol. 44(6): pp. 1707-1712.

Herbafood Press Report: Improved Fruit Fibres for Modern Food Processing. Herbafood Ingredients GmbH May/Jun. 2001.

Dreher, M. L.; Functional Properties of Dietary Fiber; Handbook of Dietary Fiber on Applied Approach; Dekker; New York, 1987, (pp. 145-146 only).

Weber, Charles W., et al.; Binding Capacity of 18 Fiber Sources for Calcium; pp. 1931-1935; J. Agric. Food Chem, 1993, 41.

Claye, Saffiatu S., et al.; Extraction and Fractionation of Insoluble fiber from five fiber sources, pp. 305-310, Food Chemistry, vol. 57, No. 2, 1996.

ConAgra Foods Nutritional Source data, Mar. 2004.

Turbak Report 2: Casebier, R. L.; Homogenized Cellulose; pp. 1-6; ITT Rayonier Inc. Olympic Research Division Report, Feb. 16, 1978.

Turback Report 3: Sandberg, Karen R.; Characterization of Homogenized Acetainier-P, pp. 1-14; ITT Rayonier Inc. Olympic Research Division Report: Aug. 27, 1979.

Turback Report 4: Sandberg, Karen R.; Pulp Homogenizing Trial at Gaulin Corporation; pp. 1-9; ITT Rayonier, Inc. Olympic Research Division Report; Sep. 4, 1979.

Turbak Report 5: Turbak, Albin F., et al.; Microfibrillated Cellulose, A New Cellulose Product: Properties, Uses and Commercial Potential, Contribution No. 223 from ITT Rayonier Inc., Research Cntr.

Turbak Report 6: Sandberg, Karen R.; Characterization of Homogenized Acetanier-P, pp. 1-14; ITT Rayonier Inc. Olympic Research Division Report; Report E 112:0-16, Nov. 1, 1979.

Turbak Report 7: Turbak, Albin F., et al.; Microfibrillated Cellulose, A New Cellulose Product: Properties, Uses and Commercial Potential.

Turbak Report 8: Asahi Chemical Industry Co., Ltd, Asahi Food Corporation & Japan Food Research Laboratories authorized by the Japanese Government; Food Material with High Water Holding Capacity: Sekicel DP300; Analysis Certificate No. 47052320-007; Jun. 6, 1994.

Turbak Report 9: Turbak, Albin F., et al.; Microfibrillated Cellulose, A New Cellulose Product: Properties, Uses and Commercial Potential Journal of Applied Polymer Science; Symposia No. 37, Proceedings of the Ninth Cellulose Conference II, 1982 by John Wiley & Sons, Inc.

"Solubility parameter values" by Eric A. Grulke in the book "Polymer Handbook", 3rd Edition, Chapter VII, p. 519-559.

C. M. Hansen: "The three-dimensional solubility parameters", J. Paint Technol. 39, 105 (1967).

Gillman K. F., Polymer Letters, vol. 5, p. 477-481 (1967).

* cited by examiner

STABILIZATION OF COSMETIC COMPOSITIONS

RELATED APPLICATIONS DATA

This application is a continuation-in-part of U.S. patent application Ser. No. 11/440,603 (filed May 25, 2006) and Ser. No. 10/969,805 (filed 20 Oct. 2004), and titled "HIGHLY REFINED CELLULOSIC MATERIALS COMBINED WITH HYDROCOLLOIDS," which are continuations-in-part of U.S. patent application Ser. No. 10/288,793, filed Nov. 6, 2002, titled "HIGHLY REFINED FIBER MASS, PROCESS OF THEIR MANUFACTURE AND PRODUCTS CONTAINING THE FIBERS."

BACKGROUND OF THE INVENTION

1. Field of the Invention

The present invention relates to the field of additives to cosmetic products, such as skin and hair cosmetic goods for human or other animal consumption, particularly cosmetic containing additives that can retain moisture and/or oil during storage or after application, while maintaining perceived feel, appearance and sensory quality in the cosmetic product.

2. Background of the Art

Cosmetic compositions are preparations externally applied to change or enhance the beauty of skin, hair, nails, lips, and eyes. The use of body paint for ornamental and religious purposes has been common among primitive peoples from prehistoric times (see body-marking). Ointments, balms, powders, and hair dyes have also been used from ancient times. Many cosmetics originated in Asia, but their ingredients and use are first recorded in Egypt; ancient tombs have yielded cosmetic jars (called kohl pots) and applicators (called cosmetic spoons). The Egyptians used kohl to darken their eyes; a crude paint was used on the face, and fingers were often dyed with henna. Greek women used charcoal pencils and rouge sticks of alkanet and coated their faces with powder, which often contained dangerous lead compounds. Beauty aids reached a peak in imperial Rome, especially chalk for the face and a rouge called focus and ladies required the services of slaves adept in their use. Many cosmetics survived the Middle Ages, and Crusaders brought back rare Eastern oils and perfumes. In the Renaissance, cosmetics, usually white-lead powder and vermilion, were used extravagantly. From the 17th century recipes and books on the toilette abounded. Professional cosmetologists began to appear, and luxurious prescriptions often included a bath in wine or milk. At its height in 1760, the use of cosmetics virtually disappeared with the advent of the French Revolution. The year 1900 saw a revival of their use, accompanied by the manufacture of beauty aids on a scientific basis in France. Since then the industry has grown to tremendous proportions with products manufactured for every conceivable use. In the United States, cosmetics intended for interstate commerce are controlled under the federal Food, Drug, and Cosmetic Act of 1938. The FDA (FD&C Act) defines cosmetics by their intended use, as "articles intended to be rubbed, poured, sprinkled, or sprayed on, introduced into, or otherwise applied to the human body . . . for cleansing, beautifying, promoting attractiveness, or altering the appearance" [FD&C Act, sec. 201(i)]. Among the products included in this definition are skin moisturizers, perfumes, lipsticks, fingernail polishes, eye and facial makeup preparations, shampoos, permanent waves, hair colors, toothpastes, and deodorants, as well as any material intended for use as a component of a cosmetic product.

SUMMARY OF THE INVENTION

A composition of matter is used as an ingredient in cosmetics or personal care products (for humans and pets) comprising at least 0.5% by weight and preferably 1-30% by weight of highly refined cellulose fiber in a cosmetic composition. Additionally present in the composition are other conventional cosmetic ingredients or personal care ingredients as known in the art. This composition may include at least colorants (dyes and pigments), lipophilic materials, aqueous materials (water and aqueous solutions), waxes, binding agents (polymers, thickening agents), emollients, emulsifiers, thickening agents, antioxidants, natural and synthetic oils and extracts, clays, ultraviolet radiation absorbers, and the like.

DETAILED DESCRIPTION OF THE INVENTION

A highly refined cellulosic materials (e.g., cellulose, modified celluloses, derivatized celluloses, hemicellulose, lignin, etc.) provides desirable properties in cosmetic compositions, improving moisture retention, oil retention and absorbance, and product stability in both storage and in application of cosmetic compositions and personal care products. A preferred highly refined cellulose product can be prepared by generally moderate treatment and still provide properties that are equivalent to or improved upon the properties of the best highly refined cellulose products produced from more intense and environmentally unfriendly processes. Fruit or vegetable cells with an exclusively parenchymal cell wall structure can be treated with a generally mild process to form highly absorbent microfibers. Cells from citrus fruit and sugar beets are particularly available in large volumes to allow volume processing to generate highly refined cellulose fibers with both unique and improved properties. These exclusively parenchymal microfibers (hereinafter referred to as EPM's) have improved moisture retention and thickening properties that enable the fibers to provide unique benefits when combined into cosmetics, including but not limited to skin creams, lotions, pancake, rouge, blush, eyeliner, eyelash extenders, lipstick, lip gloss, face paints, henna paints and hair colorants, foundation, skin softeners, skin tighteners, anti-cellulite treatments, pigment modifiers, tanning agents, sunscreens, insect repellants, massage oils, and the like.

A new process for making HRC cellulose from parenchyma cell wall products, e.g. citrus fruit and sugar beets by-products, is performed in the absence of a hydroxide soaking step. The product is able to display the same or improved water retention properties and physical properties of the more strenuously refined agricultural products of the prior art, and in some cases can provide even higher water retention values, thickening and other properties that can produce unique benefits in particular fields of use.

General descriptions of the invention include a highly refined cellulose product comprising microfibers derived from organic fiber plant mass. A preferred highly refined cellulose would contain at least 50% by weight of all fiber mass as parenchymal fiber mass, the highly refined cellulose product having a high water retention capacity, by way of non-limiting examples, of at least about 25 g $H_2O$/g dry highly refined cellulose product. The highly refined cellulose product also may have a water retention capacity of at least 50 g $H_2O$/g dry highly refined cellulose product. A highly refined cellulose material when used in this patent is defined by a fiber material that has a total dietary fiber (TDF) content greater than 15%, or greater than 20%, or greater than 25% or greater than 30% as measured by AOAC 991.43 and a water holding capacity greater than three, four or five parts water per part fiber as measured by AACC 56-30, followed literally or with the modification of testing a 2.5 gram fiber sample instead of a 5 gram fiber sample, and is less than 50%, 75% or less than 90% soluble fiber. One example of a highly refined cellulose that fits within this definition is a product from Fiberstar, Inc. (Willmar, Minn.) called Imulsi-Fi™ citrus fibers or additive. There are three types of Imulsi-Fi™ products, and they include 1) Imulsi-Fi A40, which only contains dried orange pulp, 2) Imulsi-Fi™ B40 additive, which only contains dried orange pulp and guar gum (a hydrocolloid), and 3) Imulsi-Fi™ C40, which only contains dried orange pulp and xanthan gum (a hydrocolloid). 1) The dried orange pulp in the Imulsi-Fi™ additive products is derived from parenchyma cell wall material.

Parenchymal cell walls refer to the soft or succulent tissue, which is the most abundant cell wall type in edible plants. For instance, in sugar beets, the parenchyma cells are the most abundant tissue the surrounds the secondary vascular tissues (xylem and phloem). Parenchymal cell walls contain relatively thin cell walls compared to secondary cell walls are tied together by pectin (Haard and Chism, 1996, Food Chemistry. Ed. By Fennema. Marcel Dekker NY, N.Y.) In secondary cell walls (xylem and phloem tissues), the cell walls are much thicker than parenchymal cells and are linked together with lignin (Smook). This terminology is well understood in the art.

As used in the practice of the present invention, the term "dry" or "dry product" refers to a mass that contains less than 15% by weight of fibers as water. The organic fiber mass comprises at least 50% by weight of fiber mass from organic products selected from the group consisting of sugar beets, citrus fruit, grapes, tomatoes, chicory, potatoes, pineapple, apple, carrots and cranberries. A cosmetic product or cosmetic additive may have at least 0.05 percent by weight solids in the cosmetic product or cosmetic additive of the above described highly refined cellulose product. The cosmetic product may also have at least about one-half percent, one percent or at least about two percent by weight of the highly refined cellulosic fiber of the invention.

A method for refining cellulosic material may comprise: a) soaking raw material from organic fiber plant mass comprising at least 50% by weight of all fiber mass as parenchymal fiber mass in an aqueous solution with less than 1% NaOH; b) draining the raw material and allowing the raw material to sit for a sufficient period under conditions (including ambient conditions of room temperature and pressure as well as accelerated conditions) so that the fibers and cells are softened so that shearing can open up the fibers to at least 40%, at least 50%, at least 60%, or at least 70, 80, 90 or 95% of their theoretic potential. This will usually require more that 4 hours soaking to attain this range of their theoretic potential. It is preferred that this soaking is for more than 5 hours, and preferably for at least about 6 hours. This soaking time is critical to get the materials to fully soften. When such a low alkaline concentration is used in the soaking, without the set time, the materials do not completely soften and can not be sheared/opened up to their full potential. This process produces soaked raw materials; and the process continues with refining the soaked raw material to produce refined material; and drying the soaked raw material.

The process may perform drying by many different commercial methods, although some display improved performance in the practice of the present invention. It is preferred that drying is performed, at least in part, by fluid bed drying or flash drying or a combination of the two. An alternative drying process or another associated drying step is performed at least in part by tray drying. For example, fluid bed drying may be performed by adding a first stream of organic fiber plant mass and a second stream of organic fiber plant mass into the drier, the first stream having a moisture content that is at least 10% less than the moisture content of the second stream or organic fiber plant mass. The use of greater differences in moisture content (e.g., at least 15%, at least 20%, at least 25%, at least 40%, at least 50% weight-to-weight water percent or weight-to-weight water-to-solid percent) is also within the scope of practice of the invention. In the drying method, the water may be extracted with an organic solvent prior to drying. In the two stream drying process, the second stream of organic fiber plant mass may have at least 25% water to solids content and the first stream may have less than 15% water to solids content. These processes may be practiced as batch or continuous processes. The method may use chopping and washing of the cellulose mass prior to soaking.

Another description of a useful process according to the invention may include draining and washing the soaked raw material in wash water to produce washed material; bleaching the washed material in hydrogen peroxide to produce a bleached material; and washing and filtering the bleached material to produce a filtered material.

The drying of an expanded fiber material according to the invention may use room temperature or higher air temperatures that dry the expanded fiber product and maintain the fiber material's functionalities of at least two characteristics of surface area, hydrogen bonding, water holding capacity and viscosity. This can be particularly performed with a method that uses a fluid bed dryer or flash dryer to dry the expanded or highly refined cellulosic fiber product.

The use of a flash or fluid bed dryer is an advantage over the drying methods suggested by the prior art. We have found that through the use of a fluid bed or flash dryer, low temperatures and controlled humidity are not needed to dry the materials of the present invention. In fact, although nearly any drying temperature in the fluid bed or flash dryer can be used, we have dried the product of the present invention using high air temperatures (400° F.) and attained a dry product with near equivalent functional properties after rehydration compared to the materials before drying. Additionally, using the process of the present invention, any surface area expanded cellulosic product can be dried and a functional product obtained and is not limited to parenchyma cell wall materials. The use of a fluid bed or flash dryer, the use of relatively high drying air temperatures (400 F+), and the ability to dry non parenchyma cell wall (secondary cell) and obtain a functional product is in great contrast to the relatively low temperatures, e.g. 100 C (212 F) and dryer types taught by conventional methods to dry expanded parenchymal cell wall materials. Other methods are also less energy efficient and time efficient, such as freeze drying (Gu et al, 2001).—from (Gu, L., R Ruan, P. Chen, W. Wilcke, P. Addis. 2001. Structure Function Relationships of Highly Refined Cellulose. Transactions of the ASAE. Vol 44(6):1707-1712). Freeze drying is not an economically feasible drying operation for large volumes of expanded cell wall products.

The fiber products of the invention may be rehydrated or partially rehydrated so that the highly refined cellulose product is rehydrated to a level of less than 90 g $H_2O$/g fiber mass, 70 g $H_2O$/g fiber mass, 50 g $H_2O$/g fiber mass or rehydrated to a level of less than 30 g $H_2O$/g fiber mass or less than 20 g $H_2O$/g fiber mass. This rehydration process adjusts the functionalities of the product within a target range of at least one property selected from the group consisting of water holding capacity, oil holding capacity, and viscosity and may include the use of a high shear mixer to rapidly disperse organic fiber plant mass materials in a solution. Also the method may include rehydration with soaking of the dry materials in a solution with or without gentle agitation.

Preferred areas of use include a cosmetic product to which at least 1% by weight of the organic fiber product of the invention is present in the cosmetic product. The process may enhance the stability of a cosmetic product by adding at least 0.5% by weight or 1% by weight of the highly refined cellulose products defined herein to the cosmetic products, usually in a range of from 1% to 10% by weight of the organic fiber plant mass product to the cosmetic product prior to application and then applying the cosmetic product. This process may include increasing the storage stability of any lipophilic and/or aqueous-based cosmetic product comprising adding from 1% to 10% by weight of the highly refined organic fiber plant mass product to the cosmetic product.

The basic process of the invention may be generally described as providing novel and improved fiber waste by-product from citrus fruit pulp (not the wood and stem and leaves of the trees or plant, but from the fruit, both pulp and skin) or fiber from sugar beet, tomatoes, chicory, potatoes, pineapple, apple, cranberries, grapes, carrots and the like (also exclusive of the stems, and leaves). The provided fiber mass is then optionally soaked in water or aqueous solution (preferably in the absence of sufficient metal or metallic hydroxides e.g., KOH, CaOH, LiOH and NaOH) as would raised the pH to above 9.5, preferably in the complete absence of such hydroxides (definitely less than 3.0%, less than 1.0%, more often less than 0.9%, less than 0.7%, less than 0.5%, less than 0.3%, less than 0.1%). The soaked material is then drained and optionally washed with water. This is optionally followed by a bleaching step (any bleaching agent may be used, but mild bleaching agents that will not destroy the entire physical structure of the fiber material is to be used (with hydrogen peroxide a preferred example, as well as mild chlorine bleaches). It has also been found that the bleach step is optional, but that some products require less color content and require bleaching. The (optionally) bleached material is washed and filtered before optionally being subjected to a shredding machine, such as a plate refiner which shreds the material into micro fibers. The optionally soaked, bleached, and refined material is then optionally dispersed, and homogenized at high pressure to produce HRC gel.

The HRC dispersion of the present invention is a highly viscous, semi-translucent gel. HRC embodiments comprise dried powders that are redispersable in water to form gel-like solutions. The functional characteristics of HRC are related to various properties, including water- and oil-retention capacity, average pore size, and surface area. These properties inherently relate to absorption characteristics, but the properties and benefits provided by the processes and products of the invention seem to relate to additional properties created in the practice of the invention.

The present invention also includes an aqueous HRC gel having a lignin concentration of about one to twenty percent (1 to 20%). The HRC products of the present invention exhibit a surprisingly high WRC in the range of about 20 to at least about 56 g H.sub.2O/g dry HRC. This high WRC is at least as good as, and in some cases, better than the WRC of prior art products having lower or the same lignin concentrations. The HRC products exhibit some good properties for ORC (oil retention capacity).

A general starting point for a process according to the invention is to start with raw material of sufficiently small size to be processed in the initial apparatus (e.g., where soaking or washing is effected), such as a soaker or vat. The by-product may be provided directly as a result of prior processing (e.g., juice removal, sugar removal, betaine removal, or other processing that results in the fiber by-product. The process of the present invention may also begin when raw material is reduced in size (e.g., chopped, shredded, pulverized) into pieces less than or equal to about 10.times.5 cm or 5 cm.times.2 cm. Any conventional type of manual or automated size reduction apparatus (such as chopper, shredder, cutter, slicer, etc.) can be used, such as a knife or a larger commercially-sized chopper. The resulting sized raw material is then washed and drained, thus removing dirt and unwanted foreign materials. The washed and chopped raw material is then soaked. The bath is kept at a temperature of about 20 to 100° C. The temperature is maintained within this range in order to soften the material. In one embodiment, about 100 g of chopped raw material is soaked in a 2.5 liter bath within a temperature range of about 20 to 80° C. for 10 to 90 minutes.

The resulting soaked raw material is subjected to another washing and draining. This washing and additional washing and draining tend to be more meaningful for sugar beets, potatoes, carrots (and to some degree also tomatoes, chicory, apple, pineapple, cranberries, grapes, and the like) than for citrus material. This is because sugar beets, potatoes, carrots, growing on the ground rather than being supported in bushes and trees as are citrus products, tend to pick up more materials from the soil in which they grow. Sugar beets and carrots tend to have more persistent coloring materials (dyes, pigments, minerals, oxalates, etc.) and retained flavor that also are often desired to be removed depending upon their ultimate use. In one embodiment, the soaked raw material is washed with tap water. In one other embodiment, the material is drained. This is optionally followed by bleaching the material with hydrogen peroxide at concentrations of about one (1) to 20% (dry basis) peroxide. The bleaching step is not functionally necessary to effect the citrus and grape fiber conversion to highly refined cellulose. With respect to carrots and sugar beets, some chemical processing may be desirable, although this processing may be significantly less stressful on the fiber than the bleaching used on corn-based HRC products. From our experience, some chemical step is required for sugar beets, and bleaching is one option. Using alkaline pretreatment baths is another option. Acid treatment or another bleaching agent are other options.

The material is optionally bleached at about 20 to 100° C. for about five (5) to 200 min. The bleached material is then subjected to washing with water, followed by filtering with a screen. The screen can be any suitable size. In one embodiment, the screen has a mesh size of about 30 to 200 microns.

The filtered material containing solids can then be refined (e.g., in a plate refiner, stone mill, hammer mill, ball mill, or extruder.). In one embodiment, the filtered material entering the refiner (e.g., a plate refiner) contains about four percent (4%) solids. In another embodiment, the refining can take place in the absence of water being added. The plate refiner effectively shreds the particles to create microfibers. The plate refiner, which is also called a disk mill, comprises a main body with two ridged steel plates for grinding materials. One plate, a refining plate, is rotated while a second plate remains stationary. The plates define grooves that aid in grinding. One plate refiner is manufactured by Sprout Waldron of Muncy, Pa. and is Model 12-ICP. This plate refiner has a 60 horsepower motor that operates at 1775 rpm.

Water may be fed into the refiner to assist in keeping the solids flowing without plugging. Water assists in preventing the refiner's plates from overheating, which causes materials in the refiner to burn. (This is a concern regardless of the type of grinding or shearing device used.). The distance between the plates is adjustable on the refiner. To set refining plate distances, a numbered dial was affixed to the refining plate adjustment handle. The distance between the plates was measured with a micrometer, and the corresponding number on the dial was recorded. Several plate distances were evaluated and the setting number was recorded. A variety of flow consistencies were used in the refiner, which was adjusted by varying solids feed rate. The amount of water flowing through the refiner remained constant. Samples were sent through the refiner multiple times. In one embodiment the materials are passed one or more times through the plate refiner.

The microfibers may then be separated with a centrifuge to produce refined materials. The refined materials are then diluted in water until the solids content is about 0.5 to 37%. This material is then dispersed. In one embodiment, dispersing continues until a substantially uniform suspension is obtained, about 2 to 10 minutes. The uniform suspension reduces the likelihood of plugging.

The resulting dispersed refined materials, i.e., microparticles, may then be homogenized in any known high pressure homogenizer operating at a suitable pressure. In one embodiment, pressures greater than about 5,000 psi are used. The resulting highly refined cellulose (HRC) gel may display a lignin content of about 1 to 20% by weight, depending in part upon its original content.

The absence of use of a mild NaOH soaking before the refining step in the present invention prior to high pressure homogenization does not require the use of high temperature and high pressure cooking (high temperature means a temperature above 100° C. and high pressure means a pressure above 14 psi absolute). High temperature and high pressure cooking may be used, but to the disadvantage of both economics and output of the product. This novel process further avoids the need for either mild concentrations of NaOH or of highly concentrated NaOH and the associated undesirable environmental impact of discharging waste water containing any amount of NaOH and organic compounds. The process also avoids a need for an extensive recovery system. In one embodiment, the pH of the discharge stream in the present invention is only about 8 to 9 and may even approach 7. The method of the present invention has the further advantage of reducing water usage significantly over prior art processes, using only about one third to one-half the amount of water as is used in conventional processes to produce to produce excellent HRC gel and amounts All of the mechanical operations, refining, centrifuging, dispersing, and homogenizing could be viewed as optional, especially in the case of citrus pulp or other tree bearing fruit pulps. Additionally, other shearing operations can be used, such as an extruder, stone mill, ball mill, hammer mill, etc. For citrus pulp, the only processes that are needed to produce the expanded cell structure are to dry (using the novel drying process) and then properly hydrate the raw material prior to the expanding and shearing step of the process of the invention. This simple process could also be used in other raw material sources.

Hydration is a term that means reconstituting the dried fiber back to a hydrated state so that it has functionality similar to the pre-dried material. Hydration can be obtained using various means. For instance, hydration can occur instantly by placing the dry products in a solution followed by shearing the mixture. Examples of shearing devices are a high shear disperser, homogenizer, blender, ball mill, extruder, or stone mill. Another means to hydrate the dry materials is to put the dry product in a solution and mix the materials for a period of time using gentle or minimal agitation. Hydrating dry materials prior to use in a recipe can also be conducted on other insoluble fibrous materials to enhance their functionality.

The initial slurry of fibers/cells from the EPM products is difficult to dry. There is even disclosure in the art (e.g., U.S. Pat. No. 4,413,017 and U.S. Pat. No. 4,232,049) that slurries of such processed products cannot be easily dried without expensive and time consuming processes (such as freeze drying, extended flat bed drying, and the like). Freeze drying is effective, but is not economically and/or commercially desirable. Similarly, tray dryers may be used, but the length of time, labor and energy requirements make the process costly. The slurries of the citrus and/or beet by-products may be dried economically and effectively according to the following practices of the invention. Any type of convective drying method can be used, including a flash dryer, fluid bed dryer, spray dryer, etc. One example of a dryer that can be used is a fluid bed dryer, with dry material being added to the slurry to equilibrate the moisture content in the materials. It has been found that by adding 5:1 to 1:1 dry to wet materials within the fluid bed drier improves the air flow within the drier and the material may be effectively dried. In the absence of the combination of "dry" and "wet" materials, the slurry will tend to merely allow air to bubble through the mass, without effective drying and without a true fluid bed flow in the drier. The terms wet and dry are, of course, somewhat relative, but can be generally regarded as wet having at least (>40% water/<60% solid content] and dry material having less than 20% water/80% solid content). The amounts are not as critical as the impact that the proportional amounts of materials and their respective water contents have in enabling fluid flow within the fluid bed drier. These ranges are estimates. It is always possible to use "wet" material with lower moisture content, but that would have to have been obtained by an earlier drying or other water removal process. For purpose of economy, and not for enabling manufacture of HRC microfibers according to the present invention from citrus or beet by-product, it is more economical to use higher moisture content fiber mass as the wet material. After the mixture of wet and dry materials have been fluid bed dried (which can be done with air at a more moderate temperature than is needed with flat bed dryers (e.g., room temperature air with low RH may be used, as well as might heated air). A flash drier may also be used alternatively or in combination with a fluid bed drier to effect moisture reduction from the citrus or beet by-product prior to produce a functional dry product. It would be necessary, of course, to control the dwell time in the flash drier to effect the appropriate amount of moisture reduction and prevent burning. These steps may be provided by the primary or source manufacturer, or the product may be provided to an intermediate consumer who will perform this drying step to the specification of the process that is intended at that stage.

One aspect of the drying process is useful for the drying of any expanded cellulose products, especially for the drying of highly refined cellulose fibers and particles that have been extremely difficult or expensive to dry. Those products have been successfully dried primarily only with freeze drying as a commercially viable process. That process is both expensive and energy intense. A method according to the present invention for the drying of any expanded cellulose fiber or particle product comprises drying an expanded cellulose product by providing a first mass of expanded cellulose fiber product having a first moisture content as a weight of water per weight of fiber solids; providing a second mass of expanded cellulose fiber product having a second moisture content as a weight of water per weight of fiber solids, the second moisture content being at least 20% less than said first moisture content; combining said first mass of expanded cellulose fiber product and said second mass of expanded cellulose product to form a combined mass; drying said combined mass in a drying environment to form a dried combined mass. The method may have the dried combined mass dried to a moisture content of less than 20, less than 10, less than 8, less than 5 or less than 3$H_2O$/g fiber mass. The method, by way of non-limiting examples, may use drying environments selected from the group consisting of, flash driers, fluid bed driers and combinations thereof.

The rehydration and shearing (particularly high shearing at levels of at least 10,000 $sec^{-1}$, preferably at least 15,000 sec.sup.−1, more often, greater than 20,000, greater than 30,000, greater than 40,000, and conveniently more than 50,000 $sec^{-1}$ (which is the actual shearing rate used in some of the examples) of the dry fiber product enables the resultant sheared fiber to retain more moisture and to retain moisture more strongly. It has been noted in the use of materials according to the practice of the invention that when the fiber products of the invention are rehydrated, the water activity level of rehydrated fiber is reduced in the fiber (and the fiber present in a further composition) as compared to free water that would be added to the further cosmetic composition. The high water absorbency and well dispersed nature of the product also lends itself to be an efficient thickening agent/suspending agent in cosmetics.

In another embodiment, the HRC products of the present invention possess a WRC and ORC that are at least as good as or even better than prior art products (including the Chen product) with regard to the water retention characteristics and the strength of that retention. This is true even though the products of the present invention may have a higher lignin concentration than products made using conventional processes and are dried. It is assumed that the lignin which is present has been substantially inactivated to a sufficient degree so that the undesirable clumping does not subsequently occur. Another reason for these improved properties may be due to a porous network structure that is present in the HRC products of the present invention, but is lost in prior art products due to high concentration soaking in NaOH, and which may be slightly reduced even with the mild NaOH solutions used by the Lundberg patents.

A number of unexpected properties and benefits have been provided by the highly refined cellulose microfiber product of the present invention derived from parenchymal cell material. These products are sometimes referred to herein as "exclusively parenchymal cell wall structures." This is indicative of the fact that the majority source of the material comes from the cell structures of the plants that are parenchymal cells. As noted earlier, the HRC microfibers of the invention are not produced by mild treatment of the leaves, stems, etc. of the plants (which are not only parenchymal cell wall structures, but have much more substantial cell structures). This does not mean that any source of citrus or beet cells and fibers used in the practice of the present invention must be purified to provide only the parenchymal cells. The relative presence of the more substantive cells from leaves and stems will cause approximately that relative proportion of cell or fiber material to remain as less effective material or even material that is not converted to HRC, but will act more in the nature of fill for the improved HRC microfibers of the present invention. It may be desirable in some circumstances to allow significant portions of the more substantive cells and fibers to remain or even to blend the HRC (citrus or beet parenchyma based) product of the present invention with HRC fibers of the prior art to obtain particularly desired properties intermediate those of the present invention and those of the prior art. In the primary manufacturing process of the invention (that is, the process wherein the cells that have essentially only parenchymal cell walls are converted to HRC microfibers or particles according to the mild treatment process of the present invention), the more substantive cells and fibers may be present in weight proportions of up to fifty percent (50%). It is preferred that lower concentrations of the more substantive fibers are present so as to better obtain the benefit of the properties of the HRC fibers of the present invention, so that proportions of cells having exclusively parenchymal cell walls in the batch or flow stream entering the refining process stream constitute at least 50%, at least 60%, at least 70%, at least 80%, at least 90%, at least 95%, at least 97%, at least 98%, at least 99% or preferable about 100% of the fibrous or cellular material added to the refining flow stream. The final fiber product should also contain approximately like proportions of the HRC product of the present invention with regard to other HRC additives or fiber additives.

Among the unexpected properties and benefits of the HRC materials of the present invention derived from the mild refinement of cells and fiber from citrus and beet by-product are the fact of the HRC fibers, the stability of HRC fibers from parenchymal cells, the high water retention properties, the strength of the water retention properties of the fibers, the ability of the HRC fibers to retain water (moisture) even when heated, the ability of the HRC fibers to retain water (moisture) on storage, and the ability of the HRC fibers to retain moisture in cosmetics products without promoting degradation, deterioration or spoilage of the cosmetic as compared to cosmetics with similar concentrations of moisture present in the product that is not bound by HRC fibers. The ability of the fiber materials of the present invention to retard moisture migration is also part of the benefit. This retarded water migration and water activity of water retained or absorbed by the fibers of the invention may be related to the previously discussed binding activity and binding strength of water by the fiber. As the moisture is retained away from other ingredients that are more subject to moisture-based deterioration, the materials of the invention provide significant benefits in this regard. The HRC fiber materials of the present invention provide other physical property modifying capabilities in the practice of the invention. For example, the fibers can provide thickening properties, assist in suspending or dispersing other materials within a composition, and the like. These properties are especially present in HRC fibers of the invention provided from sugar beets and citrus products.

The percentage of fiber in the final product that is desirable to provide identifiable benefits is as low as 0.01% or 0.05% or 0.1% of the total dry weight of the final product. The HRC fiber product of the invention may be used as from 0.05 to 50% by weight of the dry weight of the product, 0.5 to 40%, 1 to 40%, 1 to 30%, 1 to 25%, 1 to 20%, 1 to 15%, 1 to 10%, and 2 to 20% by weight of the dry weight of the final product.

An unexpected property is for the finished dried product to have a viscosity in a 1% solution of 1000-300,000 centipoise at 0.5 rpms when measured using a Brookfield LVDV++ viscometer (Middleboro, Mass.). An additional unexpected property is for the end processed product to have similar rheology curves as other common hydrocolloids, such as xanthan gum. The expanded fiber products of the invention are highly effective and environmentally safe viscosity enhancers.

Cosmetic Compositions and Personal Care Products

Cosmetic compositions comprise chemical formulations and compositions that are applied to the surface (usually skin, but also hair and nails) for functionality that includes at least alteration of appearance in color, texture, reflectivity, tone, smoothness, surface oil control, and other visible alterations on areas of the user. Cosmetic compositions ordinarily contain an aqueous component, as a phase or solvent, a binding component (either organic or inorganic), a lipophilic component (oil phase, oil solvent or oil dispersed particles or droplets) and other natural and synthetic additives. Other ingredients may include, but are not limited to emulsifying agents, antimicrobial agents, radiation absorbers (especially UV absorbers), free radical neutralizers (e.g., hydroquinone and other free-radical scavengers), pigments, dyes, salts, nutrients and the like. Personal Care Products have an overlap with cosmetics, and may also include cosmetics, fragrances (perfumes, oils and waters), skin care products (which may or may not have dyes, pigments or other coloration in them, distinguishing from true cosmetics), nutritional supplements (both for internal use and external use, such as moisturizing) and over-the-counter medications or applications. Specific personal care products, that tends to be classified more specifically than cosmetics include, by way of non-limiting examples, chapstick, colognes, deodorant, eyeliner, lipstick, lotion, makeup, mouthwash, pomade, perfumes, personal lubricants, shampoo, shaving cream, skin cream, lip gloss and toothpaste, to name a few.

The cosmetics may be applied for a short duration (e.g., as a wash or cleansing treatment) or for longer periods, such as days or hours.

Generic Types of Cosmetics

Lipsticks

The generic lipstick formulations, in the absence of the additional 0.01 to 30% by weight of the HRC may be described as follows. Lipstick compositions may also contain by way of non-limiting examples, from 0% and preferably 1%-70% waxes, 1%-40% pigments, 1-30% oils and 0% or 0.5-20% by weight water. Other neutral additives may complete the 100% by weight total, such as binders, extenders, fragrances, filler, radiation absorbers, and the like. In these formulations there can also be 0-50%, preferably 7-45%, more preferably 10-40%, by weight of the total composition, of particulate matter having a particle size of 0.02 to 100, preferably 0.5 to 100, microns. The particulate matter may be colored or non-colored (for example white). Suitable particulates include bismuth oxychloride, titanated mica, fumed silica, spherical silica, polymethylmethacrylate, polyethylene, polypropylene, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature. The particulates may also include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof. Preferably the composition will contain both pigmented and non-pigmented particulates. Obviously the percentage of pigments used in the particulate phase will depend on the type of cosmetic being formulated. Color cosmetics generally have a much higher concentration of color than other types of cosmetics. Generally the weight ratio of pigmented to non-pigmented particulates range from 1:50 to 50:1. It should be noted that particulates that are white or have no color are considered non-pigmented particulates in accordance with the invention, while particulates which exhibit color other than white are considered pigmented particulates in accordance with the invention.

The lipstick composition may also contain 0-70%, preferably 1-30%, more preferably 1-25% by weight of a cosmetically acceptable natural or synthetic wax. The waxes that can be used are solid or semi-solid waxes having a melting point of 30 to 120.degree. C. and generally includes animal waxes, plant waxes, mineral waxes, silicone waxes, synthetic waxes, and petroleum waxes.

Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series. In the preferred embodiment of the invention the waxes are polymers of ethylene and/or propylene.

Hair Conditioners

In addition to the ranges of 1-25% polymer, 0-2% cross-linking agent, and 0.5-5% blocking agent, hair conditioning agents in accordance with the invention generally comprise 0.1-20% cationic conditioning agent, 0.1-30% fatty alcohol, 0.001-10% nonionic surfactant, and 5-95% water. The most suitable cationic conditioning agents are cationic polymers, quaternary ammonium salts or the salts of fatty amines.

Shampoo

In addition to containing the ranges of 1-25% polymer, 0-2% cross-linking agent, shampoo compositions in accordance with the invention comprise 0.5-30% of a cleansing surfactant and 10-95% water. Suitable cleansing surfactants include anionic, amphoteric, nonionic, or zwitterionic surfactants. Fragrances, alcohols, antifungal agents, Ultraviolet radiation absorbers, and other typical additives may also be present with the composition and the added HRC.

Mascara

Mascara compositions in accordance with the invention generally contain, in addition to the ranges of 1-25% polymer, 0-2% cross-linking agent, 0.1-30% wax, 0.1-50% oil, 0.1-50% particulate matter, and 0.1-10% emulsifier. Suitable waxes, oils, and particulate matter are also useful additives of the types mentioned above.

Face Makeup

Face makeup compositions in accordance with the invention generally are water-in-oil or oil-in-water emulsion foundation compositions, or color cosmetics such as makeup, blush, concealer, and the like. Typically, emulsions may comprise 10-95% water and 10-95% oil, in addition to pigments. Anhydrous compositions such as blush, eyeshadow, and the like may comprise 1-95% particulates, 0.5-30% oil, and other ingredients. Suitable particulates, oils and particulates are as mentioned above.

Aqueous Phase

The composition may, by way of non-limiting examples, furthering the other descriptions herein, comprise water or a mixture of water and of hydrophilic organic solvents, for instance alcohols and especially linear or branched lower monoalcohols containing from 2 to 5 carbon atoms, for instance ethanol, isopropanol or n-propanol, polyols, for instance glycerol, diglycerol, propylene glycol, sorbitol or pentylene glycol, and polyethylene glycols. The hydrophilic phase may also contain hydrophilic $C_2$ ethers and $C_2$-$C_4$ aldehydes.

Water or a mixture of water and of hydrophilic organic solvents may be present in the composition according to the invention in a content ranging from 0 to 90%, especially 0.1% to 90% by weight, preferably from 0 to 60% by weight and especially 0.1% to 60% by weight, relative to the total weight of the composition.

The medium may comprise a liquid organic phase in which water is dispersed or emulsified, on condition that the red interference pigment is in major amount in the aqueous phase.

Film-Forming Agents

The medium may comprise a film-forming agent, especially a film-forming polymer, for example in a content ranging from 1% to 90% depending on the nature of the composition. The term "film-forming agent" means an agent capable of forming, by itself or in the presence of an auxiliary film-forming agent, a macroscopically continuous film that adheres to keratin materials, and preferably a cohesive film, and better still a film whose cohesion and mechanical properties are such that the said film may be isolable and manipulable in isolation, for example when the said film is prepared by pouring onto a non-stick surface, for instance a Teflon-coated or silicone-coated surface. The film-forming agent may or may not be present in the aqueous phase. This agent may be in dispersion or in solution in the aqueous phase, while avoiding excessively unfavourably affecting the refractive index. The film-forming agent may be a film-forming polymer.

Film-Forming Polymer

The term "film-forming" polymer means a polymer capable, by itself or in the presence of an auxiliary film-forming agent, of forming a continuous film that adheres to a support, especially to keratin materials, preferably a cohesive film and better still a film whose cohesion and mechanical properties are such that the said film may be isolated from the said support. Among the film-forming polymers that may be used in the composition of the present invention, mention may be made of synthetic polymers, of free-radical type or of polycondensate type, and polymers of natural origin, and mixtures thereof.

Film-forming polymers that may be mentioned in particular include acrylic polymers (including methacrylic), polyurethanes, polysiloxane, polyesters, polyamides, polyureas and cellulose-based polymers, for instance nitrocellulose. These film-forming polymers may be divided into four classes, as a function of their solubility with regard to an aqueous phase or a liquid fatty phase.

In one embodiment, the film-forming polymer is at least one polymer chosen from the group comprising: film-forming polymers that are soluble in a liquid fatty phase of the composition, in particular liposoluble polymers, film-forming polymers that are dispersible in a liquid fatty phase of the composition, in particular polymers in the form of non-aqueous dispersions of polymer particles, preferably dispersions in silicone oils or hydrocarbon-based oils, aqueous dispersions of film-forming polymer particles, often known as "latices", water-soluble film-forming polymers.

According to another embodiment of the invention, the film-forming polymer is silicone-based and may be chosen from polymers with a non-silicone organic backbone grafted with monomers containing a polysiloxane. According to another embodiment of the invention, the film-forming polymer is silicone-based and is chosen from silicone polymers grafted with non-silicone organic monomers. These polymers may be liposoluble, lipodispersible, water-soluble or dispersible in aqueous medium, where appropriate.

For obvious reasons, the amounts of film-forming agent in the compositions according to the invention may vary significantly, especially with regard to the nature of the film-forming agent under consideration and also with regard to the qualities desired for the composition incorporating it. The composition may comprise, as polymer, a dispersion of particles of a grafted ethylenic polymer in a liquid fatty phase. The term "ethylenic" polymer means a polymer obtained by polymerization of ethylenically unsaturated monomers, that is monomers that have at least one ethylenically unsaturated group (C=C) that is involved in the polymerization process.

The dispersion of grafted ethylenic polymer is especially free of stabilizing polymer different from the said grafted polymer, such as those described in EP 749 747 and described hereinbelow, and the particles of grafted ethylenic polymer are therefore not surface-stabilized with such additional stabilizing polymers. The grafted polymer is therefore dispersed in the liquid fatty phase in the absence of additional surface stabilizer for the particles.

The term "grafted" polymer means a polymer having a backbone comprising at least one side chain that is pendent or located at the end of a chain, and preferably pendent.

Advantageously, the grafted ethylenic polymer comprises an ethylenic backbone that is insoluble in the said liquid fatty phase, and side chains covalently bonded to the said backbone, which are soluble in the liquid fatty phase. The grafted ethylenic polymer is especially a non-crosslinked polymer. In particular, the polymer is obtained by polymerization of monomers comprising only one polymerizable group.

The grafted ethylenic polymer is, for example, a grafted acrylic polymer. The grafted ethylenic polymer may especially be obtained by free-radical polymerization in an organic polymerization medium: of at least one ethylenic monomer, in particular of at least one acrylic monomer and optionally of at least one additional non-acrylic vinyl monomer, to form the said insoluble backbone; and of at least one macromonomer comprising a polymerizable end group to form the side chains, the said macromonomer having a weight-average molar mass of greater than or equal to 200 and the content of polymerized macromonomer representing from 0.05% to 20% by weight of the polymer.

The composition may comprise a liquid fatty phase that may contain the organic polymerization medium for the grafted ethylenic polymer. The organic liquid dispersion medium, corresponding to the medium in which the grafted polymer is supplied, may be identical to the polymerization medium. However, the polymerization medium may be totally or partially replaced with another organic liquid medium. This other organic liquid medium may be added, after polymerization, to the polymerization medium. The said polymerization medium is then totally or partially evaporated.

The liquid fatty phase may contain liquid organic compounds other than those present in the dispersion medium. These other compounds are chosen such that the grafted polymer remains in dispersed form in the liquid fatty phase.

The organic liquid dispersion medium may be present in a liquid fatty phase of the composition according to the invention due to the introduction into the composition of the dispersion of grafted polymer obtained.

Such a liquid fatty phase may comprise, preferably predominantly, one or more liquid organic compounds (or oils) as defined below. In particular, the composition may comprise a liquid fatty phase that may be a non-aqueous liquid organic phase that is immiscible with water at room temperature (25° C.).

The term "liquid organic compound" means a non-aqueous compound that is in liquid form at room temperature (25° C.) and therefore flows under its own weight.

Among the liquid organic compounds or oils that may be present in the liquid organic dispersion medium, mention may be made of: liquid organic compounds, especially silicone-based or non-silicone-based, having a global solubility parameter according to the Hansen solubility space of less than or equal to 18 (MPa)$^{1/2}$ and preferably less than or equal to 17 (MPa)$^{1/2}$, monoalcohols having a global solubility parameter according to the Hansen solubility space of less than or equal to 20 (MPa)$^{1/2}$, and mixtures thereof.

The global solubility parameter .delta. according to the Hansen solubility space is defined in the article "Solubility parameter values" by Eric A. Grulke in the book "Polymer Handbook", 3rd Edition, Chapter VII, p. 519-559, by the relationship: $.delta.=(.delta._D{}^2+.delta._P{}^2+.delta._H{}^2).^{-1/2}$. in which delta$_D$ characterizes the London dispersion forces arising from the formation of dipoles induced during molecular impacts, delta$_P$ characterizes the Debye interaction forces between permanent dipoles, and delta$_H$ characterizes the forces of specific interactions (such as hydrogen bonding, acid/base, donor/acceptor, etc.).

The definition of solvents in the solubility space according to Hansen is described in the article by C. M. Hansen: "The three-dimensional solubility parameters", J. Paint Technol. 39, 105 (1967). Among the liquid organic compounds, especially silicone-based or non-silicone-based, having a global solubility parameter according to the Hansen solubility space of less than or equal to 18 (MPa)$^{1/2}$, mention may be made of liquid fatty substances, especially oils, which may be chosen from natural or synthetic, carbon-based, hydrocarbon-based, fluoro and silicone oils, which are optionally branched, alone or as a mixture. Among these oils, mention may be made of plant oils formed from fatty acid esters and from polyols, in particular triglycerides, such as sunflower oil, sesame oil or rapeseed oil, or esters derived from acids or alcohols containing a long chain (i.e. a chain containing from 6 to 20 carbon atoms), in particular the esters of formula RCOOR' in which R represents a higher fatty acid residue containing from 7 to 19 carbon atoms and R' represents a hydrocarbon-based chain containing from 3 to 20 carbon atoms, such as palmitates, adipates and benzoates, in particular diisopropyl adipate.

Mention may also be made of linear, branched and/or cyclic alkanes that may be volatile, and in particular liquid paraffin, liquid petroleum jelly or hydrogenated polyisobutylene, isododecane or "Isopars", volatile isoparaffins. Mention may also be made of esters, ethers and ketones.

Mention may also be made of silicone oils such as polydimethylsiloxanes and polymethylphenylsiloxanes, optionally substituted with aliphatic and/or aromatic groups, which are optionally fluorinated, or with functional groups such as hydroxyl, thiol and/or amine groups, and volatile silicone oils, which are especially cyclic.

In particular, mention may be made of volatile and/or non-volatile, optionally branched silicone oils.

As non-silicone-based liquid organic compounds with a global solubility parameter according to the Hansen solubility space of less than or equal to 18 (MPa)$^{1/2}$, mention may be made in particular of: linear, branched or cyclic esters containing at least 6 carbon atoms, especially 6 to 30 carbon atoms; ethers containing at least 6 carbon atoms, especially 6 to 30 carbon atoms; and ketones containing at least 6 carbon atoms, especially 6 to 30 carbon atoms.

The expression "liquid monoalcohols having a global solubility parameter according to the Hansen solubility space of less than or equal to 20 (MPa)$^{1/2}$, means aliphatic fatty liquid monoalcohols containing from 6 to 30 carbon atoms, the hydrocarbon-based chain not comprising a substitution group. Monoalcohols according to the invention that may be mentioned include oleyl alcohol, decanol, octyldodecanol and linoleyl alcohol.

When the composition comprises a non-silicone liquid fatty phase, the macromonomers present in the grafted polymer are advantageously carbon-based macromonomers as described below. In particular, when the composition comprises a non-silicone liquid fatty phase, the grafted polymer present in the composition is advantageously a non-silicone grafted polymer.

The term "non-silicone grafted polymer" means a grafted polymer mainly containing a carbon-based macromonomer and optionally containing not more than 7% by weight and preferably not more than 5% by weight of silicone macromonomer, or even being free of silicone macromonomer.

When the cosmetic composition according to the invention comprises a silicone-based liquid fatty phase, the macromonomers present in the grafted polymer are advantageously silicone-based macromonomers as described below.

In particular, when the liquid fatty phase is a silicone-based liquid fatty phase, the grafted polymer present in the composition is advantageously a silicone-based grafted polymer.

The term "silicone-based grafted polymer" means a grafted polymer predominantly containing a silicone-based macromonomer and optionally containing up to 7% by weight and preferably up to 5% by weight of carbon-based macromonomer, or even being free of carbon-based macromonomer.

Monomers

The choice of monomers constituting the backbone of the polymer, of macromonomers, the molecular weight of the polymer, and the proportion of the monomers and macromonomers may be made as a function of the liquid organic dispersion medium so as advantageously to obtain a dispersion of particles of grafted polymers, in particular a stable dispersion, this choice possibly being made by a person skilled in the art.

The term "stable dispersion" means a dispersion that is not liable to form a solid deposit or to undergo liquid/solid phase separation, especially after centrifugation, for example at 4000 rpm for 15 minutes.

The grafted ethylenic polymer forming the particles in dispersion thus comprises a backbone that is insoluble in the said dispersion medium and a portion that is soluble in the said dispersion medium.

The grafted ethylenic polymer may be a random polymer. According to the invention, the term "grafted ethylenic polymer" means a polymer that may be obtained by free-radical polymerization: of one or more ethylenic monomer(s); with one or more macromonomer(s), in an organic polymerization medium.

According to the invention, the term "grafted acrylic polymer" means a polymer that may be obtained by free-radical polymerization: [0175] of one or more acrylic monomer(s), and optionally of one or more additional non-acrylic vinyl monomer(s); with one or more macromonomer(s), in an organic polymerization medium.

Advantageously, the acrylic monomers represent from 50% to 100% by weight, preferably from 55% to 100% by weight (especially from 55% to 95% by weight) and preferentially from 60% to 100% by weight (especially from 60% to 90% by weight) of the mixture of acrylic monomers+ optional non-acrylic vinyl monomers.

In particular, the acrylic monomers are chosen from monomers whose homopolymer is insoluble in the dispersion medium under consideration, i.e. the homopolymer is in solid (or non-dissolved) form at a concentration of greater than or equal to 5% by weight at room temperature (20.degree. C.) in the said dispersion medium.

According to the invention, the expression "macromonomer containing a polymerizable end group" means any polymer comprising on only one of its ends a polymerizable end group capable of reacting during the polymerization reaction with acrylic monomers and optionally the additional non-acrylic vinyl monomers constituting the backbone. The macromonomer makes it possible to form the side chains of the grafted acrylic polymer. The polymerizable group of the macromonomer may advantageously be an ethylenically unsaturated group capable of free-radical polymerization with the monomers constituting the backbone.

The term "carbon-based macromonomer" means a non-silicone-based macromonomer and especially an oligomeric macromonomer obtained by polymerization of ethylenically unsaturated non-silicone-based monomer(s), and mainly by polymerization of acrylic and/or non-acrylic vinyl monomers.

The term "silicone-based macromonomer" means an organopolysiloxane macromonomer and in particular a polydimethylsiloxane macromonomer. In particular, the macromonomer is chosen from macromonomers whose homopolymer is soluble in the dispersion medium under consideration, i.e., fully dissolved at a concentration of greater than or equal to 5% by weight and at room temperature in the said dispersion medium.

Thus, the grafted acrylic polymer comprises a backbone (or main chain) consisting of a sequence of acrylic units resulting from the polymerization especially of one or more acrylic monomers and of side chains (or grafts) derived from the reaction of the macromonomers, the said side chains being covalently bonded to the said main chain.

The backbone (or main chain) is insoluble in the dispersion medium under consideration, whereas the side chains (or grafts) are soluble in the said dispersion medium.

In the present patent application, the term "acrylic monomers" means monomers chosen from (meth)acrylic acid, (meth)acrylic acid esters (also known as (meth)acrylates), and (meth)acrylic acid amides (also known as (meth)acrylamides). These acrylic monomers may contain substituents such as polyoxyethylene and/or polyoxypropylene, the said polyoxyalkylene group consisting of a repetition of 5 to 30 oxyalkylene units; a cyclic alkyl group containing from 3 to 6 carbon atoms, the said group possibly comprising in its chain one or more hetero atoms chosen from O, N and S, and/or possibly comprising one or more substituents chosen from OH and halogen atoms (F, Cl, Br or I); methyl, ethyl, propyl, butyl, isobutyl, methoxyethyl, ethoxyethyl, methoxypolyoxyethylene (350 OE), trifluoroethyl, 2-hydroxyethyl, 2-hydroxypropyl, dimethylaminoethyl, diethylaminoethyl or dimethylaminopropyl group; (ii) (meth)acrylamides, 1,1-dimethyl-3-oxobutyl group and the like.

Among these acrylic monomers, those that may be mentioned most particularly are methyl, ethyl, propyl, butyl and isobutyl(meth)acrylates; methoxyethyl or ethoxyethyl (meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate, 2-hydroxyethyl acrylate; dimethylaminopropylmethacrylamide; and the salts thereof; and mixtures thereof.

In particular, the acrylic monomers are chosen from methyl acrylate, methoxyethyl acrylate, methyl methacrylate, 2-hydroxyethyl methacrylate, acrylic acid and dimethylaminoethyl methacrylate, and mixtures thereof.

Among the additional non-acrylic vinyl monomers that may be mentioned are: vinyl esters of the following formula: $R_6$—COO—CH=CH$_2$ in which: $R_6$ represents a linear or branched alkyl group containing from 1 to 6 atoms, or a cyclic alkyl group containing from 3 to 6 carbon atoms and/or an aromatic group, for example of benzene, anthracene or naphthalene type; non-acrylic vinyl monomers comprising at least one carboxylic acid, phosphoric acid or sulfonic acid function, such as crotonic acid, maleic anhydride, itaconic acid, fumaric acid, maleic acid, styrenesulfonic acid, vinylbenzoic acid or vinylphosphoric acid, and the salts thereof; non-acrylic vinyl monomers comprising at least one tertiary amine function, such as 2-vinylpyridine or 4-vinylpyridine; and mixtures thereof.

Advantageously, the acrylic monomers present in the grafted polymer comprise at least (meth)acrylic acid and at least one monomer chosen from the (meth)acrylates and (meth)acrylamides described previously in points (i) and (ii). Preferably, the acrylic monomers comprise at least (meth)acrylic acid and at least one monomer chosen from $C_1$-$C_3$ alkyl(meth)acrylates. (Meth)acrylic acid may be present in a content of at least 5% by weight, especially ranging from 5% to 80% by weight, preferably of at least 10% by weight, especially ranging from 10% to 70% by weight, and preferentially of at least 15% by weight, especially ranging from 15% to 60% by weight, relative to the total weight of the polymer.

Among the salts that may be mentioned are those obtained by neutralization of acid groups with mineral bases such as sodium hydroxide, potassium hydroxide or ammonium hydroxide, or organic bases such as alkanolamines, for instance monoethanolamine, diethanolamine, triethanolamine or 2-methyl-2-amino-1-propanol. Alternatively, the salts may be formed by neutralization of tertiary amine units, for example using a mineral or organic acid. Among the mineral acids that may be mentioned are sulfuric acid, hydrochloric acid, hydrobromic acid, hydriodic acid, phosphoric acid and boric acid. Among the organic acids that may be mentioned are acids comprising one or more carboxylic, sulfonic or phosphonic groups. They may be linear, branched or cyclic aliphatic acids, or alternatively aromatic acids. These acids may also comprise one or more hetero atoms chosen from O and N, for example in the form of hydroxyl groups. Acetic acid or propionic acid, terephthalic acid, and citric acid and tartaric acid may especially be mentioned.

According to one embodiment of the invention, the alternative and optional grafted ethylenic polymers contain no additional non-acrylic vinyl monomers as described above. In this embodiment, the insoluble backbone of the grafted ethylenic polymer is formed solely from acrylic monomers as described previously.

It is understood that these non-polymerized acrylic monomers may be soluble in the dispersion medium under consideration, but the polymer formed with these monomers is insoluble in the dispersion medium.

According to one particular embodiment of the invention, the grafted ethylenic polymer (if present) may be obtained by free-radical polymerization in an organic polymerization medium: of a main acrylic monomer chosen from $C_1$-$C_3$ alkyl(meth)acrylates, alone or as a mixture, and optionally of one or more additional acrylic monomers chosen from (meth)acrylic acid, methacrylic acid and alkyl(meth)acrylates and salts thereof, to form the said insoluble backbone; and of at least one silicone-based macromonomer comprising a polymerizable end group, as defined previously.

Main acrylic monomers that may be used include methyl acrylate, methyl methacrylate, ethyl acrylate, ethyl methacrylate, n-propyl acrylate, n-propyl methacrylate, isopropyl acrylate and isopropyl methacrylate, and mixtures thereof. Methyl acrylate, methyl methacrylate and ethyl methacrylate may be mentioned most particularly. The additional acrylic monomers may be chosen from: acrylic acids and (meth)acrylic acids and their salts and derivatives. Among these additional acrylic monomers, mention may be made most particularly of (meth)acrylic acid, methoxyethyl or ethoxyethyl(meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate and 2-hydroxyethyl acrylate, the salts thereof, and mixtures thereof. Acrylic acid and methacrylic acid may be mentioned most particularly (these may also be referred to in the art as acryloyl polymers and methacryloyl polymers).

Macromonomers

The macromonomers comprise at one of the ends of the chain a polymerizable end group capable of reacting during the polymerization with the acrylic monomers and optionally the additional vinyl monomers, to form the side chains of the grafted ethylenic polymer. The said polymerizable end group may in particular be a vinyl or (meth)acrylate (or (meth)-acryloxy) group, and preferably a (meth)acrylate group. The macromonomers are preferably chosen from macromonomers whose homopolymer has a glass transition temperature (Tg) of less than or equal to 25° C., especially ranging from −100° C. to 25° C. and preferably ranging from −80° C. to 0° C. The macromonomers have a weight-average molar mass of greater than or equal to 200, preferably greater than or equal to 300, preferentially greater than or equal to 500 and more preferentially greater than 600. Preferably, the macromonomers have a weight-average molar mass (Mw) ranging from 200 to 100 000, preferably ranging from 500 to 50 000, preferentially ranging from 800 to 20 000, more preferentially ranging from 800 to 10 000 and even more preferentially ranging from 800 to 6000. In the present patent application, the weight-average (Mw) and number-average (Mn) molar masses are determined by liquid gel permeation chromatography (THF solvent, calibration curve established with linear polystyrene standards, refractometric detector).

Carbon-based macromonomers that may in particular be mentioned include: (i) homopolymers and copolymers of linear or branched $C_8$-$C_{22}$ alkyl acrylate or methacrylate, containing a polymerizable end group chosen from vinyl or (meth)acrylate groups, among which mention may be made in particular of: poly(2-ethylhexyl acrylate) macromonomers with a mono(meth)acrylate end group; poly (dodecyl acrylate) or poly(dodecyl methacrylate) macromonomers with a mono(meth)acrylate end group; poly (stearyl acrylate) or poly(stearyl methacrylate) macromonomers with a mono(meth)acrylate end group. Such macromonomers are described in particular in the patents EP 895 467 and EP 096 459, and in the article by Gillman K. F., Polymer Letters, Vol 5, page 477-481 (1967).

Also useful are macromonomers based on poly(2-ethylhexyl acrylate) or poly(dodecyl acrylate) with a mono(meth) acrylate end group; (ii) polyolefins containing an ethylenically unsaturated end group, in particular containing a (meth)acrylate end group. Examples of such polyolefins that may be mentioned in particular include the following macromonomers, it being understood that they have a (meth) acrylate end group: polyethylene macromonomers, polypropylene macromonomers, macromonomers of polyethylene/ polypropylene copolymer, macromonomers of polyethylene/polybutylene copolymer, polyisobutylene macromonomers; polybutadiene macromonomers; polyisoprene macromonomers; polybutadiene macromonomers; poly(ethylene/butylene)-polyisoprene macromonomers.

Such macromonomers are described in particular in U.S. Pat. No. 5,625,005, which described ethylene/butylene and ethylene/propylene macromonomers containing a (meth) acrylate reactive end group. Also useful are the poly(ethylene/butylene) methacrylate such as those sold under the name Kraton®, such as Liquid L-1253 by Kraton Polymers, Inc.

Silicone-based macromonomers that may be particularly useful and may include polydimethylsiloxanes containing mono(meth)acrylate end groups. Silicone-based macromonomers that may be used include monomethacryloxypropyl polydimethylsiloxanes such as those sold under the name PS560-K6 by the company United Chemical Technologies Inc. (UCT) or under the name MCR-M17 by Gelest Inc.

More particularly, the polymerized macromonomer (constituting the side chains of the grafted polymer) represents from 0.1% to 15% by weight, preferably from 0.2% to 10% by weight and more preferably from 0.3% to 8% by weight, relative to the total weight of the polymer.

As particularly preferred grafted ethylenic polymer dispersed in a non-silicone-based liquid fatty phase, it is possible to use those obtained by polymerization: of methyl acrylate and of a polyethylene/polybutylene macromonomer containing a methacrylate end group (especially Kraton® L-1253), in particular in a solvent chosen from isododecane, isononyl isononanoate, octyldodecanol, diisostearyl malate or a $C_{12}$-$C_{15}$ alkyl benzoate (such as Finsolv Tenn.); of methoxyethyl acrylate and of a polyethylene/polybutylene macromonomer containing a methacrylate end group (especially Kraton® L-1253), in particular in isododecane; of methyl acrylate/methyl methacrylate monomers and of a polyethylene/polybutylene macromonomer containing a methacrylate end group (especially Kraton L-1253), in particular in isododecane; of methyl acrylate/acrylic acid monomers and of a polyethylene/polybutylene macromonomer containing a methacrylate end group (especially Kraton® L-1253), in particular in isododecane; of methyl acrylate/ dimethylaminoethyl methacrylate monomers and of a polyethylene/polybutylene macromonomer containing a methacrylate end group (especially Kraton® L-1253), in particular in isododecane; of methyl acrylate/2-hydroxyethyl methacrylate monomers and of a polyethylene/polybutylene macromonomer containing a methacrylate end group (especially Kraton® L-1253), in particular in isododecane.

As particularly envisaged grafted acrylic polymer dispersed in a silicone-based liquid fatty phase, it is possible to use those obtained by polymerization: of methyl acrylate and of the monomethacryloyl-oxypropyl polydimethylsiloxane macromonomer with a weight-average molecular weight ranging from 800 to 6000, in particular in decamethylcyclopentasiloxane or phenyl trimethicone; of methyl acrylate, acrylic acid and the monometh-acryloxypropyl polydimethylsiloxane macromonomer with a weight-average molecular weight ranging from 800 to 6000, in particular in decamethylcyclopentasiloxane or phenyl trimethicone.

In particular, the grafted polymer has a weight-average molar mass (Mw) of between 10 000 and 300 000, especially between 20 000 and 200 000 and better still between 25 000 and 150 000.

By virtue of the abovementioned characteristics, in a given organic dispersion medium, the polymers have the capacity of folding over on themselves, thus forming particles of substantially spherical shape, the periphery of these particles having the deployed side chains, which ensure the stability of these particles. Such particles resulting from the characteristics of the grafted polymer have the particular feature of not aggregating in the said medium and thus of being self-stabilized and of forming a particularly stable polymer particle dispersion. In particular, the grafted ethylenic polymers of the dispersion are capable of forming nanometer-sized particles, with a mean size ranging from 10 to 400 nm and preferably from 20 to 200 nm. As a result of this very small size, the grafted polymer particles in dispersion are particularly stable and therefore have little susceptibility to form aggregates. The dispersion of grafted polymer may thus be a dispersion that is stable and does not form sediments when it is placed at room temperature (25° C.) for an extended period (for example 24 hours). In particular, the dispersion of grafted polymer particles has a solids content (or dry extract) of polymer of from 40% to 70% by weight of solids and especially from 45% to 65% by weight.

Production Process

The dispersion of grafted polymer particles may be prepared via a process comprising a free-radical copolymerization step, in an organic polymerization medium, of one or more acrylic monomers as defined above with one or more macromonomers as defined above.

The liquid organic dispersion medium may be identical to or different from the polymerization medium. The copolymerization may be performed conventionally in the presence of a polymerization initiator. The polymerization initiators may be free-radical initiators. In general, such a polymerization initiator may be chosen from organic peroxide compounds such as dilauroyl peroxide, dibenzoyl peroxide or tert-butyl peroxy-2-ethylhexanoate; diazo compounds such as azobisisobutyronitrile or azobisdimethylvaleronitrile. The reaction may also be initiated using photoinitiators or with radiation such as UV or neutrons, or with plasma. In general, to perform this process, at least a portion of the organic polymerization medium, a portion of the additional acrylic and/or vinyl monomers, which will constitute the insoluble backbone after polymerization, all of the macromonomer (which will constitute the side chains of the polymer) and a portion of the polymerization initiator are introduced into a reactor whose size is suitable for the amount of polymer to be prepared. At this stage of introduction, the reaction medium forms a relatively homogeneous medium.

The reaction medium is then stirred and heated up to a temperature to obtain polymerization of the monomers and macromonomers. After a certain time, the initially homogeneous and clear medium leads to a dispersion of milky appearance. A mixture consisting of the remaining portion of monomers and of polymerization initiator is then added. After an adequate time during which the mixture is heated with stirring, the medium stabilizes in the form of a milky dispersion, the dispersion comprising polymer particles stabilized in the medium in which they have been created, the said stabilization being due to the presence, in the polymer, of side chains that are soluble in the said dispersion medium.

The grafted polymer may be present in the composition according to the invention in a solids content (or active material content) ranging from 1% to 70% by weight, better still from 5% to 60% by weight, preferably ranging from 6% to 45% by weight and better still ranging from 8% to 40% by weight, relative to the total weight of the composition. In one embodiment, the film-forming polymer is an organic film-forming polymer that is soluble in a liquid fatty phase of the composition, especially in one or more oils of the composition.

In this case, it is referred to as a liposoluble polymer. The liposoluble polymer may be of any chemical type and may especially be chosen from:

a) liposoluble, amorphous homopolymers and copolymers of olefins, of cycloolefins, of butadiene, of isoprene, of styrene, of vinyl ethers, esters or amides, or of (meth)acrylic acid esters or amides comprising a linear, branched or cyclic $C_{4-50}$ alkyl group and which are preferably amorphous. The preferred liposoluble homopolymers and copolymers are obtained from monomers chosen from the group consisting of isooctyl (meth)acrylate, isononyl(meth)acrylate, 2-ethylhexyl (meth)acrylate, lauryl(meth)acrylate, isopentyl(meth) acrylate, n-butyl(meth)acrylate, isobutyl(meth) acrylate, methyl(meth)acrylate, tert-butyl(meth)

acrylate, tridecyl(meth)acrylate and stearyl(meth) acrylate, or mixtures thereof. Examples that will be mentioned include the alkyl acrylate/cycloalkyl acrylate copolymer sold by Phoenix Chem. under the name Giovarez AC-5099 mL, and vinylpyrrolidone copolymers, such as copolymers of a $C_2$-$C_{30}$ and in particular $C_3$ to $C_{22}$ alkene, and combinations thereof, may be used. As examples of VP copolymers that may be used in the invention, mention may be made of copolymers of VP/vinyl laurate, VP/vinyl stearate, butylated polyvinylpyrrolidone (PVP), VP/hexadecene, VP/triacontene or VP/acrylic acid/lauryl methacrylate.

Particular liposoluble copolymers that may be mentioned include:

i) acrylic-silicone grafted polymers containing a silicone backbone and acrylic grafts or containing an acrylic backbone and silicone grafts, such as the product sold under the name SA 70.5 by 3M and described in U.S. Pat. No. 5,725,882, U.S. Pat. No. 5,209,924, U.S. Pat. No. 4,972,037, U.S. Pat. No. 4,981,903, U.S. Pat. No. 4,981,902 and U.S. Pat. No. 5,468,477, and in U.S. Pat. No. 5,219,560 and EP 0 388 582;

ii) liposoluble polymers belonging to one of the classes described above and bearing fluoro groups, in particular those described in U.S. Pat. No. 5,948,393 and the alkyl (meth)acrylate/perfluoroalkyl (meth)acrylate copolymers described in patents EP 0 815 836 and U.S. Pat. No. 5,849,318;

iii) polymers or copolymers resulting from the polymerization or copolymerization of an ethylenic monomer, comprising one or more ethylenic bonds, which are preferably conjugated (or diene). As polymers or copolymers resulting from the polymerization or copolymerization of an ethylenic monomer, it is possible to use vinyl, acrylic or methacrylic copolymers.

In one embodiment, the film-forming polymer is a block copolymer comprising at least one block consisting of styrene units or styrene derivatives (for example methylstyrene, chlorostyrene or chloromethylstyrene). The copolymer comprising at least one styrene block may be a diblock or triblock copolymer, or even a multiblock copolymer, in starburst or radial form. The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, a methacrylate (MA) block or a combination of these blocks. The copolymer comprising at least one block consisting of styrene units or styrene derivatives may be a diblock or triblock copolymer, and in particular of the polystyrene/polyisoprene or polystyrene/polybutadiene type, such as those sold or manufactured under the name "Luvitol HSB" by BASF, and those of the polystyrene/copoly(ethylene-propylene) type or alternatively of the polystyrene/copoly(ethylene-butylene) type, such as those sold or manufactured under the brand name "Kraton" by Shell Chemical Co. or Gelled Permethyl 99A by Penreco may be used. Examples that may be mentioned include Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58 (blend of triblock and of starburst block polymer), Gelled Permethyl 99A-753-59 (blend of triblock and of starburst block polymer), Versagel 5970 and Versagel 5960 from Penreco (blend of triblock and of starburst polymer in isododecane).

Styrene-methacrylate copolymers may also be used, such as the polymers sold under the references OS 129880, OS 129881 and OS 84383 from Lubrizol, Inc. (styrene-methacrylate copolymer). In one embodiment, the film-forming polymer is chosen from copolymers of a vinyl ester (the vinyl group being directly attached to the oxygen atom of the ester group and the vinyl ester having a saturated, linear or branched hydrocarbon-based radical of 1 to 19 carbon atoms, linked to the carbonyl of the ester group) and of at least one other monomer, which may be a vinyl ester (other than the vinyl ester already present), an .alpha.-olefin (containing from 8 to 28 carbon atoms), an alkyl vinyl ether (the alkyl group of which contains from 2 to 18 carbon atoms) or an allylic or methallylic ester (containing a saturated, linear or branched hydrocarbon-based radical of 1 to 19 carbon atoms, linked to the carbonyl of the ester group).

These copolymers may be partially crosslinked using crosslinking agents, which may be either of the vinyl type or of the allylic or methallylic type, such as tetraallyloxyethane, divinylbenzene, divinyl octanedioate, divinyl dodecanedioate, and divinyl octadecanedioate. Examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate-/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene crosslinked with 0.2% divinylbenzene, and allyl propionate/allyl stearate, crosslinked with 0.2% divinylbenzene.

Liposoluble film-forming polymers that may also be mentioned include liposoluble copolymers, and in particular those resulting from the copolymerization of vinyl esters containing from 9 to 22 carbon atoms or of alkyl acrylates or methacrylates, the alkyl radicals containing from 10 to 20 carbon atoms. Such liposoluble copolymers may be chosen from copolymers of polyvinyl stearate, polyvinyl stearate crosslinked with divinylbenzene, with diallyl ether or with diallyl phthalate, polystearyl(meth)acrylate copolymers, polyvinyl laurate and polylauryl(meth)acrylate, these poly (meth)acrylates possibly being crosslinked with ethylene glycol dimethacrylate or tetraethylene glycol dimethacrylate.

The liposoluble copolymers defined above are known and described especially in the art and may have a weight-average molecular weight ranging from 2000 to 500 000 and preferably from 4000 to 200 000. As examples of liposoluble polymers that may be used in the invention, mention may be made of polyalkylenes and $C_2$-$C_{20}$ alkene copolymers, in particular polybutene.

b) amorphous and liposoluble polycondensates, in particular not comprising any groups donating hydrogen interactions, in particular aliphatic polyesters containing C.sub.4-50 alkyl side chains or polyesters resulting from the condensation of fatty acid dimers, or even polyesters comprising a silicone-based segment in the form of a block, graft or end group, as defined in patent application FR 0 113 920, and c) film-forming polymer may be chosen in particular from cellulose-based polymers such as nitrocellulose, cellulose acetate, cellulose acetobutyrate, cellulose acetopropionate or ethylcellulose, or from polyurethanes, acrylic polymers, vinyl polymers, polyvinyl butyrals, alkyd resins, resins derived from aldehyde condensation products, such as arylsulfonamide-formaldehyde resins, for instance toluenesulfonamide-formaldehyde resin, and arylsulfonamide epoxy resins. Film-forming polymers that may especially be used include nitrocellulose RS (Hercules, Inc.) toluenesulfonamide-formaldehyde resins (e.g., Ketjentflex MS80 from Akzo or "Santolite MHP" and "Santolite MS80" from Faconnier or "Resimpol 80" from Pan Americana, the alkyd resin "Beckosol Ode 230-70-E" company Dainippon Chemicals, the acrylic resin "Acryloid B66" from Rohm & Haas, and the polyurethane resin "Trixene PR 4127" from the Baxenden). Silicone resins, which are generally soluble or swellable in silicone oils. These resins are crosslinked polyorganosiloxane polymers.

The term "resin" means a three-dimensional structure. In one embodiment, the silicone resin is chosen from silsesquioxanes and siloxysilicates. In one embodiment, the silicone resin is chosen from siloxysilicates. The film-forming silicone resin may be chosen, for example, from the resins Wacker 803 and 804, available from Wacker Silicone Corporation, and GE 1170-002 available from General Electric.

In another embodiment, the silicone resin is chosen from silsesquioxanes Not all polymethylsilsesquioxanes are film-forming. For example, the polymethylsilsesquioxanes such as Tospearl™ from Toshiba or KMP 590 from Shin-Etsu are highly insoluble in oils and, as a result, are inefficient film-forming agents. The molecular mass of these polymethylsilsesquioxanes is difficult to determine.

An example of a polymethylsilsesquioxane that may be used according to the invention is Belsil PMS MK (also known as MK resin) available from Wacker Chemie. Polymethylsilsesquioxane is a polymer mainly consisting of $CH_3SiO_{3/2}$ repeating units (units T) and also possibly containing up to about 1% (on a weight or molar basis) of $(CH_3)_2.2SiO_2/2$ (units D).

The polymethylsilsesquioxanes that are suitable for use in the present invention comprise KR-220L, available from Shin-Etsu. The structure of KR-220L consists essentially of silicone units T ($CH_3SiO_{3/2}$) with Si—OH or silanol end units. There were no units D.

Example 1

A lipstick formulation would be made with 0.5 grams Imulsi-Fi™ B40 particulate additive, 55.5 grams beeswax, 20 grams organic red pigment, 2 grams organic blue pigment, 20 grams vinyl acetate/allyl stearate polymer, and 2 grams oleyl alcohol.

Example 2

A lotion formulation would be made with 0.5 grams Imulsi-Fi™ B40 particulate additive, 0.2 grams ultraviolet radiation absorber, 5 grams water-soluble acrylic polymer, 1 grams oleyl alcohol and 93.3 grams water.

Example 3

An eyeliner formulation would be made with 1.5 grams Imulsi-Fi™ B40 particulate additive, 0.2 grams ultraviolet radiation absorber, 65 grams water-soluble acrylic polymer, 1 grams linoleic alcohol, 31.3 grams black pigment and 1.0 grams water.

Example 4

The objective of this experiment was to create a natural lotion using Imulsi-Fi™, water, and oil using a shear emulsification process and use a combination of oils useful for their medical properties and make a smooth finished product that could be suitable as a lotion. The following formula was used and the mixing procedure is shown below.

| Ingredients | wt (g) | % | part/300FG |
|---|---|---|---|
| Imulsi-Fi C40 additive | 50 | 6.22 | 1 |
| Cranberry Seed Oil | 10 g | 1.24 | 0.2 |
| Safflower Seed Oil | 190 g | 23.63 | 3.8 |
| Water | 550 | 68.41 | 11 |
| Potassium Sorbate (preservative) | 4 | 0.49 | 0.08 |
| Total | 804 | ~100 | |

Here is the mixing procedure used in the formula shown above.
1. Combine 50 g Imulsi-Fi C40 with 50 g oil {45 g safflower oil+5 g cranberry oil}
2. Shear at low speed in a 2-speed ("Waring Commercial Lab Blender") ~1 min
3. Dissolve 4 g potassium sorbate in 300 g water, and add to mixture
4. Shear at low speed (~2 min)
5. Add additional 150 g oil {145 g safflower oil+5 g cranberry oil}
6. Shear at low speed (~30 sec)
7. Add additional 150 g water
8. Shear at low speed (~1 min)
9. Add additional 100 g water
10. Shear at low speed (~1 min)

The resulting product was a smooth emulsion that could be used as a cosmetic lotion and useful for its antioxidant and other health properties as a result of the combinations of oils used. The Imulsi-Fi C40 products stabilize and thicken the emulsion and make the appearance of the finished product similar to that of a typical lotion.

Example 5

A similar product was made as shown in Example 4 except a grape seed oil was used instead of cranberry oil. The formula and mixing procedure is shown below. Formula [entitled "Grape Seed Lotion"]

| Ingredients | wt (g) | % | part/300FG |
|---|---|---|---|
| Imulsi-Fi ™ C40 additive | 50 | 6.22 | 1 |
| Grape Seed Oil | 10 g | 1.24 | 0.2 |
| Safflower Seed Oil | 190 g | 23.63 | 3.8 |
| Water | 550 | 68.41 | 11 |
| Potassium Sorbate (preserv.) | 4 | 0.49 | 0.08 |
| Total | 804 | ~100 | |

Mixing Procedure
1. Combine 50 g Imulsi-Fi™ C40 additive with 50 g oil {45 g safflower oil+5 g grape seed oil}
2. Shear at low speed in a 2-speed ("Waring Commercial Lab Blender") ~1 min 3. Dissolve 4 g potassium sorbate in 300 g water, and add to mixture
4. Shear at low speed (~2 min)
5. Add additional 150 g oil {145 g safflower oil+5 g grape seed oil}
6. Shear at low speed (~30 sec)
7. Add additional 150 g water
8. Shear at low speed (~1 min)
9. Add additional 100 g water Example 6

Oils that are useful for the immunosuppressant properties can also be included in the lotions made with the Imulsi-Fi™ products and a formula is shown and mix procedure below. Formula [entitled "Immuno-Viva Lotion"]

| Ingredients | wt (g) | % | part/300FG |
|---|---|---|---|
| Imulsi-Fi C40 | 50 | 6.22 | 1 |
| Immuno-Viva Oil | 10 g | 1.24 | 0.2 |
| Safflower Seed Oil | 190 g | 23.63 | 3.8 |
| Water | 550 | 68.41 | 11 |
| Potassium Sorbate (preserv.) | 4 | 0.49 | 0.08 |
| Total | 804 | ~100 | |

Mix Procedure:
1. Combine 50 g Imulsi-Fi™ C40 with 50 g oil {45 g safflower oil+5 g Immuno-Viva oil}
2. Shear at low speed in a 2-speed ("Waring Commercial Lab Blender") ~1 min
3. Dissolve 4 g potassium sorbate in 300 g water, and add to mixture
4. Shear at low speed (~2 min)
5. Add additional 150 g oil {145 g safflower oil+5 g Immuno-Viva oil}
6. Shear at low speed (~30 sec)
7. Add additional 150 g water
8. Shear at low speed (~1 min)
9. Add additional 100 g water Example 7

The advantage of the Imulsi-Fi™ particle products is that they are able to stabilize a wide variety of solutions that contain both lipid and aqueous parts. For instance, a wide number of lipid based oils can be used or even a single oil can be used. In this example, only soybean oil is used and the result is a stable emulsion that can used as a base in many cosmetic, nutraceutical, or health care related products. The formula and mixing procedure are shown below.

| Ingredients | wt (g) | % |
|---|---|---|
| Imulsi-Fi C40 | 50 | 6.2 |
| soy bean oil | 200 | 24.8 |
| water | 550 | 68.4 |
| potassium sorbate (preserv.) | 4 | 0.5 |
| Total | 804 | ~100 |

Mix Procedure
1. Combine 50 g Imulsi-Fi™ C40 additive with 50 g soy bean oil
2. Shear at low speed in a 2-speed ("Waring Commercial Lab Blender") ~1 min
3. Dissolve 4 g potassium sorbate in 300 g water, and add to mixture
4. Shear at low speed (~2 min)
5. Add additional 150 g soy bean oil
6. Shear at low speed (~30 sec)
7. Add additional 150 g water
8. Shear at low speed (~1 min)
9. Add additional 100 g water
10. Shear at low speed (~1 min), Although specific materials and specific numbers are disclosed herein, those numbers and materials are merely examples of the generic scope of the invention and are not intended to limit the claims beyond their actual recitation. All references cited herein and U.S. Pat. No. 7,074,300 are incorporated herein by reference in their entireties.

Example 8

Imulsi-Fi™ additive's unique expanded cell structure permit to formulate oil in water (O/W) as well as water in oil emulsion (W/O). In this example a Night Cream (O/W) was formulated with Imulsi-Fi A40 at 5%.

| Phase | INCI Name | w/w % |
|---|---|---|
| A | Aqua | 100 |
| | Glycerin | 5.0 |
| | Sodium Chloride | 0.5 |
| B | Imulsi-Fi ™ A40 additive | 5.0 |
| | Cetyl-Stearyl Alcohol | 2.0 |
| | *Persea Gratissima* (Avocado)oil | 5.0 |
| | Caprylic/Capric triglyceride | 5.0 |
| | Isohexadecane | 9.0 |
| | *Copernica Cerifera* (Carnauba) Wax | 1.2 |
| | Hydrogenated vegetable oil | 0.8 |
| | Hydrogenated Soy Fixed oil | 2.0 |
| C | Methylisothiazolinone | 5.0 |

Procedure
1—Mix phase A ingredients
2—Mix phase B ingredients
3—Stir A into B and homogenize for 1 min.
4—Cool down to 40° C. and homogenize again for 2 minutes
5—Add C when temperature reaches 30° C.

Example 9

In this example, a Skin Milk (W/O) was created with Imulsi-Fi B40 additive at 5%. Formula and mixing procedure are shown below.

| Phase | INCI Name | w/w % |
|---|---|---|
| A | Aqua | 100 |
| | Propylene Glycol | 3.0 |
| B | Imulsi-Fi ™ B40 additive | 5.0 |
| | Cetyl-Stearyl Alcohol | 1.5 |
| | Cetearyl Stearate | 0.8 |
| | Dicaprylyl Carbonate | 6.0 |
| | Isopropyl Palmitate | 3.0 |
| | Myristyl Myristate | 2.0 |
| | C12-15 Alkyl Benzoate | 3.0 |
| | *Persea Gratissima* (Avocado)oil | 0.8 |
| C | Methylisothiazolinone | 5.0 |

Procedure
1—Mix phase A and B

2—Stir A into B and heat to 80° C.
3—Homogenize at 70° C. and 50° C.
4—At 30° C. add part C under stirring.

Example 10

In this example an emulsion was made that contained 2% salicylic acid. Due to the strong emulsifying power of Imulsi-Fi® additive products, there was no need to add a co-emulsifier in order to obtain stable emulsions. Formula and procedure are shown below.

|  | Test 1 | Test 2 |
|---|---|---|
| Mineral oil | 20 | 20 |
| Water | 73 | 73 |
| Salicylic acid | 2 | 2 |
| Imulsi-Fi ™ A40 additive | 5 |  |
| Imulsi-Fi ™ B40 additive |  | 5 |
| Total | 100 | 100 |

Procedure:
1—Heat mineral oil, Imulsi-Fi™ additives and salicylic acid to 80° C.
2—Add water under constant stirring.

Example 11

The stability of Imulsi-Fi™ additive products was tested in 4 different oils: mineral oil, avocado oil, olive oil and safflower oil with and without a co-emulsifier (Cetyl-Stearyl Alcohol). Emulsions without co-emulsifier were composed of 20% oil, 5% Imulsi-Fi additive, 75% water. Emulsions with an emulsifier were composed of 20% oil, 75% water, 4.5% Imulsi-Fi additive, and 0.5% co-emulsifier. Samples were kept at 40° C. and stability was evaluated at day 9 of the study as shown in table below.

|  | Mineral oil | Avocado oil | Olive oil | Safflower oil |
|---|---|---|---|---|
| Imulsi-Fi ™ A40 additive | + | + | − | + |
| Imulsi-Fi A40 additive + coemulsifier | + | + | − | + |
| Imulsi-Fi B40 additive | + | + | + | + |
| Imulsi-Fi B40 additive + coemulsifier | + | + | + | + |
| Xyliance ™ additive * | − | + | + | + |

* with coemulsifier
+ stable
− non stable

Example 12

Extreme temperatures accelerate physic-chemistry reactions, quickening the alteration of products. The thermo stability of a cream made with Imulsi-Fi™ C40 additive was evaluated at 4° C., 20° C., 37° C., 45° C., and 54° C. at initial day and at weeks 4, 8 and 12. The parameters evaluated were pH, viscosity, and product stability. PH and viscosity values remained stable throughout the study. In regards to cream stability, no instability was seen for any of the samples except a slight darkening in the sample kept at 54° C. in the week 8 and 12.

Example 13

The study described in the Example 12 was identically carried out in a cream made with Imulsi-Fi A40 additive and 1% Keltrol RD. No significant differences were observed in the pH and viscosity values throughout the study. Furthermore, any of the samples showed any sign of instability except for the sample kept at 45° C. in the week 8 of the study which became slightly dark.

Example 14

A study was conducted in order to test the stability of Imulsi-Fi™ additive at low temperatures and under the stress of consecutive free/thaw cycle. The experiment was conducted in samples made at initial day and samples that were 90 days old at the moment of conducting this experiment. Three sets of samples were made and stored under the following conditions:
1) Freeze at T=−18° C. for 24 hours and thaw at T=5° C. for 24 hours
2) Freeze at T=−18° C. for 72 hours and thaw at T=24° C. for 24 hours
3) 2 Cycles of t=24 h at T=−18° C. and T=24° C.

A close examination of the samples did not show any significant variation in the viscosity, appearance, color and odor of the creams neither of the ones made at the initial day nor at the ones that were 3 month old. Table below show no significant variations in humidity, ph, and viscosity at 10 rpm of the creams at initial day and 3 month old samples.

| Analysis | Sample made Initial day | Sample 3 month old |
|---|---|---|
| Humidity | 68.56% | 66.62% |
| pH | 5.17 | 4.70 |
| Viscosity at 10 rpm | 47030 | 41991 |

Example 15

The table below shows the ingredients that were used to make an Antiperspirant/deodorant and the procedure that was followed.

| Phase | INCI Name | w/w % |
|---|---|---|
| A | Triglyceride | 16.0 |
|  | Meadowfoam Seed Oil | 4.0 |
|  | Almond Oil | 2.0 |
|  | Cetyl Alcohol | 14.0 |
|  | Imulsi-Fi ™ A40 additive | 3.0 |
| B | Cyclo-Dimethicone | 30.0 |
|  | Glycerin | 2.0 |
|  | Aluminun Chlorohydrate | 15.0 |
|  | Talcum | 13.0 |
| C | Fragance Oil | 1.0 |

Procedure:
1—Mix phase A and heat to 70° C.
2—Cool down to 60° C. and add phase B ingredients one by one slowly and under constant stirring.
3—Add phase C and stir.

Example 16

The objective of this experiment was to create a creamy shaving foam using Imulsi-Fi A40 additive. The following formula was used and the mixing procedure is shown below.

| Phase | INCI Name | w/w % |
|---|---|---|
| A | Water | 61.1 |
| | Ceterareth-20 | 3.0 |
| | Imulsi-Fi ™ A40 additive | 0.5 |
| B | PEG-7 Glyceryl Cocoate | 2.0 |
| | Coco Betaine | 14.0 |
| | Grapeseed Oil | 2.0 |
| | Glycerin | 5.0 |
| | Dimethicone | 0.5 |
| C | Water | 1.0 |
| | Allantoin | 0.2 |
| | Paraben-DU | 1.0 |
| | Fragance | 0.2 |

Procedure:
1—Mix phase A, heat up to 70° C. and remove from heat
2—Add phase B one by one to phase A by gentle stirring
3—Dissolve the allantoin in the water o phase C and add to phase A/B
4—Add the remaining ingredients of phase C and stir.

Example 17

This example demonstrates how to use Imulsi-Fi B40 in a hair conditioner product.

| Phase | INCI Name | w/w % |
|---|---|---|
| A | Water | 81.4 |
| | Glycerin | 2.0 |
| B | Imulsi-Fi ™ B40 additive | 2.5 |
| | Meadowfoam Seed Oil | 3.0 |
| | Olive Oil | 1.0 |
| C | Cyclo-Dimethicone | 1.0 |
| | Vitamin E Acetate | 0.5 |
| | Phenoxyethanol | 1.5 |
| | Fragance | 0.5 |
| | Citric Acid | 0.1 |

Procedure
1—Mix phase A.
2—Mix phase B and heat up to 71° C.
3—Add phase B to phase A and stir well
4—Remove from the heat.
5—Cool to 40° C. then add phase C in order stirring after each ingredient
6—Adjust the pH to 4-5.5 with citric acid.

Method technology and improvement technology according to the present invention may include, for example, a method of stabilizing a cosmetic product or personal care product against effects of exposure to humidity comprising the steps of:
a) providing a highly refined cellulose fiber;
b) combining the highly refined cellulose fiber with a liquid carrier that is either hydrophilic or hydrophobic to form a first additive composition;
c) combining the first additive composition formed in step b) with at least one ingredient selected from the class of polymers, waxes and oils to form a cosmetic product or personal care product having a final composition; and
d) storing the cosmetic product or personal care product.

In these methods, after step b), the additive composition may be further combined, respectively, with second composition comprising a hydrophobic composition or a hydrophilic composition, and the first additive composition and the second composition are blended to form a second additive composition, and the second additive composition is used in step c). Furthermore, the addition of the highly refined composition with all other ingredients combined into the cosmetic product or personal care product can produce a final composition of the cosmetic product or personal care product that retains at least 3% more water within the final composition of the cosmetic product or personal care product when exposed to standard conditions of 20 C, 50% relative humidity and 760 mm Hg pressure for 12 hours as compared to a composition of a cosmetic product or personal care product identical to the final composition, except for the absence of any highly refined cellulose. This test procedure can be readily performed without undue experimentation by having a thickness of the final composition and comparison composition being between 2-5 mm, with 50 mm$^2$ exposed surface area to the ambient test standard environment.

With a more solid material, such as a lipstick or mascara, the test period may be longer (e.g., 72 hours), but effectively test results will show a similar benefit, moisture (water) retention in the product without deterioration of general product properties, that is, the product will retain original properties for longer when containing the highly refined cellulose than when an otherwise identical composition is made without highly refined cellulose. By a more solid material (e.g., lipstick, mascara, etc.) is meant a material that when stored in a open container with only support of a flat surface (e.g., a petri dish) will retain its shape under 1 G forces for at least 24 hours. According to practices of the present technology, such a material will retain at least 3% more water within the final composition of the cosmetic product or personal care product when exposed to standard conditions of 20° C., 50% relative humidity and 760 mm Hg pressure for 72 hours as compared to a composition of a cosmetic product or personal care product identical to the final composition, except for the absence of any highly refined cellulose. The 72 hour test, without requiring the shape stability of the more solid material, may also be used with liquid materials. The percent greater retention of water in the product may also be required to be 5%, 8% 10% or more in those tests.

Surprisingly, the water absorbent HRC fibers of the present invention provide oil stabilization with cosmetic or personal care products. A test for oil stabilization and under conditions similar to those mentioned above, but preferably using accelerated testing because oil movement within the composition would be slower under most ambient conditions can be described as follows.

A method is provided for oil stabilizing a cosmetic product or personal care product against excessive oil migration within the composition. A method may be practiced by first determining overall oil concentration of the final composition (which should be at least 35 and preferably at least 5% by total weight to maximize benefits of the present technology, and amounts of at least 10% or at least 15%, at least 20% and at least 25% by weight will show increased benefits. The final composition will be tested for stability under accelerated conditions, rather than standard room conditions. For example, the composition or article (e.g., lip stick or mascara) will be placed in an open container at temperatures below the boiling point of liquids in the composition, for example at temperatures of 30 C, 40 C, or 50 C at 1 G and 760 mm Hg air pressure. Humidity is less important for this test, but it will be assumed to be 50% RH, which will be part of the standard. The total overall concentration of oil in the composition will be used as a base for the test. Because oil tends to migrate to the surface of any composition, the following test is based upon changes in oil composition on the surface of the final composition containing HRC and does not need a comparison to a composition without HRC therein. Steps in the process would comprise:
- a) providing a highly refined cellulose fiber;
- b) combining the highly refined cellulose fiber with a liquid carrier that is either hydrophilic or hydrophobic to form a first additive composition;
- c) combining the first additive composition formed in step b) with at least one ingredient selected from the class of polymers, waxes and oils to form a cosmetic product or personal care product having a final composition, at least one of the first additive composition and the second additive composition containing oil such that the personal care product or cosmetic product contains the at least 3% total oil (or more as indicated above); and
- d) storing the cosmetic product or personal care product in an open container, such as a petri dish;
- e) the storage is done under the above defined test conditions (e.g., 30 C, for 72 hours at 50% RH, 760 mm Hg and 1 G) preferably in a relatively flat exposure profile of a surface of the material, such as a puddle for liquids, and a pancake for more solid materials (as previously discussed), with at least 1 mm in depth, preferably at least 5 mm in depth of the material;
- f) after passage of the time period for the test (e.g., 24 hours, 48 hours, 72 hours or more, as defined in the test), a sample of the topmost region of the puddle or pancake is removed (siphoned, sliced, sectioned or otherwise physically removed) and the oil concentration measured;
- g) the absolute amount of oil in the sample may be read, if oil is not observed or sensed as having oozed onto the surface (showing failure of stabilization if present in an extreme amount where quantitative testing would not be needed, and the percentage of oil in the removed sample determined.

The efficacy of the product is based on the relative similarity of oil concentration in the removed sample as compared to the original material. One easy way to determine relative amounts of oil is to simply weigh the sample taken, extract (leach, or otherwise isolate oil) and compare the amount of removed oil to the original weight of the sample. Leaching may remove additional materials (plasticizer, fragrances, dyes, monomers, etc.) and those should be accounted for in the simple mathematics performed on the analysis. The level of skill needed to perform this task is moderate, for example a B.S. in Chemistry with laboratory work in quantitative analysis would be able to perform this task with little or no additional supervision. Accuracy within ±0.5% is sufficient, although accuracy within ±0.2% is preferred. The present technology has shown that through a depth of 0.5 mm in a thickness of 5.0 mm, the concentration of oil in the cosmetic and/or personal care products often can be kept ±3%, ±5%, ±8%, ±10% of the original concentration and promote stability with regard to oil migration.

The method may be practiced wherein after step b), the additive composition is further combined, respectively, with second composition comprising a hydrophobic composition or a hydrophilic composition, and the first additive composition and the second composition are blended to form a second additive composition, and the second additive composition is used in step c). The addition of the highly refined cellulose to the composition with all other ingredients combined into the cosmetic product or personal care product produces a final composition of the cosmetic product or personal care product that stabilizes the surface of the composition to no more than 3% more total oil within the final composition of the cosmetic product or personal care product within 0.5 mm of the surface of the test sample when exposed to accelerated conditions of 50° C., 50% relative humidity and 760 mm Hg pressure for 12, or 24 or 48 or 72 hours as compared to an original composition as compounded.

This can be further described as a method of oil-migration stabilizing a cosmetic product or personal care product against effects of internal migration or blushing of oil:
- a) providing a highly refined cellulose fiber;
- b) combining the highly refined cellulose fiber with a liquid carrier that is either hydrophilic or hydrophobic to form a first additive composition;
- c) combining the first additive composition formed in step b) with at least one ingredient selected from the class of polymers, waxes and oils to form a cosmetic product or personal care product having a final composition with at least 3% by total weight of oil; and
- d) storing the cosmetic product or personal care product.

Where the cosmetic product or personal care product has a thickness of 5 mm, when stored in a open container under conditions of 30° C., 50% relative humidity and 760 mm Hg pressure for 72 hours will retain a composition having a percentage of total oil/weight of composition to a depth of 0.5 mm that is no more than 3% greater in concentration of oil/total weight of the composition as compared to an original oil/total weight percentage of the cosmetic product or personal care product. That is, if the original composition in a thickness of 5 mm contained 10% oil, the upper 0.5 mm of the sample would not exceed 1.03×10% or never exceed 10.3% oil/total weight of composition.

The use of the high-content parenchymal wall products produces from fruit and vegetable matter with high-parenchymal wall content is particularly effective in this stabilizing performance.

What is claimed:

1. A method of oil-migration stabilizing a cosmetic product or personal care product against effects of internal migration or blushing of oil:
- a) providing a highly refined cellulose fiber composition consisting of plant cells at least 50% by weight of the plant cells derived from cells having exclusively parenchymal cell walls, highly refined cellulose fiber of the highly refined cellulose fiber composition having a water holding capacity greater than five parts water per part fiber and being free of acid bleaching and NaOH chemical processing;
- b) combining the highly refined cellulose fiber with a liquid carrier that is either hydrophilic or hydrophobic to form a first additive composition;
- c) combining the first additive composition formed in step b) with at least one ingredient selected from the class of polymers, waxes and oils to form a cosmetic product or personal care product having a final composition with at least 3% by total weight of oil; and
- d) storing the cosmetic product or personal care product.

2. The method of claim 1 wherein parenchymal cells consist essentially of citrus fruit cells free of chemical treatment and free of treatment with NaOH and the cosmetic product or personal care product has a thickness of 5 mm, when stored in a open container under conditions of 30° C., 50% relative humidity and 760 mm Hg pressure for 72 hours will retain a composition having a percentage of total oil/weight of composition to a depth of 0.5 mm that is no more than 3% greater in concentration of oil/total weight of the composition as compared to an original oil/total weight percentage of the cosmetic product or personal care product.

3. The method of claim 1 wherein the parenchymal cells consist essentially of citrus fruit cells that have not been exposed to NaOH solutions during refinement.

4. A method of moisture stabilizing a cosmetic product or personal care product against effects of exposure to humidity comprising the steps of:
   a) providing a highly refined cellulose fiber composition comprising citrus fruit parenchymal cells free of chemical treatment and free of treatment with NaOH, the highly refined cellulose fiber, derived from plant cells having exclusively parenchymals, having a water holding capacity greater than five parts water per part fiber and being free of acid bleaching or NaOH chemical processing;
   b) combining the highly refined cellulose fiber with a liquid carrier that is either hydrophilic or hydrophobic to form a first additive composition;
   c) combining the first additive composition formed in step b) with at least one ingredient selected from the class of polymers, waxes and oils to form a cosmetic product or personal care product having a final composition; and
   d) storing the cosmetic product or personal care product.

* * * * *